US006426351B1

(12) United States Patent
Weichselbaum et al.

(10) Patent No.: US 6,426,351 B1
(45) Date of Patent: Jul. 30, 2002

(54) CHELERYTHRINE-BASED THERAPIES FOR CANCER

(75) Inventors: Ralph R. Weichselbaum, Chicago, IL (US); Donald W. Kufe, Wellesley, MA (US); Steven J. Chmura, Chicago; Mary E. Dolan, Oak Park, both of IL (US)

(73) Assignees: Dana-Farber Cancer, Inc., Boston, MA (US); Arch Development Corporation, Chicago, IL (US)

( * ) Notice: Subject to any disclaimer, the term of this patent is extended or adjusted under 35 U.S.C. 154(b) by 0 days.

(21) Appl. No.: 09/637,816

(22) Filed: Aug. 11, 2000

(51) Int. Cl.$^7$ .............................................. A61K 31/44
(52) U.S. Cl. ...................................................... 514/280
(58) Field of Search ........................................ 514/280

(56) References Cited

U.S. PATENT DOCUMENTS

| | | | |
|---|---|---|---|
| 209,331 A | | 10/1878 | Daniel |
| 433,257 A | | 7/1890 | Ryan |
| 2,344,830 A | | 3/1944 | Mohs et al. |
| 4,145,412 A | | 3/1979 | Ladanyi .................... 424/58 |
| 4,376,115 A | | 3/1983 | McCrorey .................. 424/145 |
| 4,406,881 A | | 9/1983 | Ladanyi .................... 424/49 |
| 5,137,912 A | * | 8/1992 | Teng et al. ................. 514/463 |
| 5,324,520 A | * | 6/1994 | Dunn et al. ................ 424/435 |
| 5,747,502 A | * | 5/1998 | Hanaoka et al. ........... 514/280 |
| 5,786,362 A | * | 7/1998 | Krongrad .................. 514/280 |
| 5,821,072 A | * | 10/1998 | Schwartz et al. ........... 435/15 |
| 6,025,365 A | * | 2/2000 | Weichselbaum et al. .... 514/298 |
| 6,171,786 B1 | * | 1/2001 | Shtil et al. ..................... 435/6 |
| 6,284,783 B1 | * | 9/2001 | Zhou et al. ................. 514/414 |

OTHER PUBLICATIONS

Blagosklonny et al., "Taxol induction of p21$^{WAF1}$ and p53 requires c–raf–1," *Cancer Res.*, 55:4623–4626, 1995.
Brachman et al., "p53 mutation does not correlate with radiosensitivity in 24 head and neck cancer cell lines," *Cancer Res.*, 53:3667–3669, 1993.
Carroll et al., "p53 oncogene mutations in three human prostate cancer cell lines," *Prostate*, 23:123–134, 1993.
Chen et al., "Suppression of Bcl–2 messenger RNA production may mediate apoptosis after ionizing radiation, tumor necrosis factor α, and ceramide," *Cancer Res.*, 55:991–994, 1995.
Chmura et al., Decreasing the apoptotic threshold of tumor cells through protein kinase C inhibition and sphingomyelinase activation increases tumor killing by ionizing radiation, *Cancer Res.*, 57:4340–4347, 1997.
Chmura et al., "Cross–talk between ceramide and PKC activity in the control of apoptosis," *Adv Exp Med Biol*;406:39–55, 1996a.
Chmura et al., "Protein Kinase C inhibition induces apoptosis and ceramide production through a neutral sphingomyelinase," *Cancer Res.*, 56:2711–2714, 1996.

Datta et al., "Activation of the CPP32 Protease in apoptosis induced by 1–β–D–Arabinofuranosylcytsine and other DNA–damaging agents," *Blood*, 88:1936–1943, 1996.
Datta et al., "Overexpression of Bcl–$x_L$ by cytotoxic drug exposure confers resisitance to ionizing radiation–induced internucleosomal DNA fragments," *Cell Growth Differ.*, 6:363–370, 1995.
Datta et al., "Activation of a CrmA–insensitive, p35–sensitive pathway in ionizing radiation–induced apoptosis," *J. Biol. Chem.* 272:1965–1969, 1997.
Emoto et al., "Proteolytic activation of protein kinase C δ by an ICE–like protease in apoptotic cells," *EMBO J.*, 14:6148–6156, 1995.
Grant et al., "Modulation of 1–[beta–D–arabinofuranosyl] cytosine–induced apoptosis in human myeloid leukemia cells by staurosporine and other pharmacological inhibitors of protein kinase C," *Oncol. Res.*, 6:87–99, 1994.
Gray et al., "Alkaloid, lignan and sterol constituents of zanthoxylum simulans," *Planta Medica* 39:209, 1980.
Gupta et al., "Thyroid–stimulating hormone activates phospholipase D in FRTL–5 thyroid cells via stimulation of protein kinase C," *Endocrinology*, 136:3794–3799, 1995.
Hallahan et al., "The interaction between recombinant human tumor necrosis factor and radiation in 13 human tumor cell lines," *Int. J. Rad. Onc. Biol.*, 19:69–74, 1990.
Hallahan et al., "C–jun and Egr–1 participate in DNA synthesis and cell survival in response to ionizing radiation exposure," *J. Biol. Chem.*, 270:30303–30309, 1995.
Hallahan et al., "Membrane–derived second messenger regulates x–ray–mediated tumor necrosis factor α gene induction," *Proc. Natl. Acad. Sci., USA.*, 91:4897–4901, 1994.
Hallahan et al., "Inhibition of protein kinases sensitizes human tumor cells to ionizing radiation," *Radiat. Res.*, 129:345–350, 1992.
Herbert et al., "Chelerythrine is a potent and specific inhibitor of protein kinase C," *Biochem. Biophys. Res. Commun.*, 172:993–999, 1990.
Jarvis and Kolesnick, "Ceramide and the induction of apoptosis," *Clinical. Cancer Research*, 2:1–6, 1996.
Jarvis et al., "Induction of apoptosis and potentiation of ceramide–mediated cytotoxicity by sphingoid bases in human myeloid leukemia cells," *J Biol Chem*, 271(14):8275–8284, 1996.
Jarvis et al., "Induction of apoptotic DNA damage and cell death by activation of the sphingomyelin pathway," *Proc. Natl. Acad. Sci. USA*, 91:73–77, 1994.
Jarvis et al., "Induction of apoptotic DNA fragmentation and cell death in HL–60 human promyelocytic leukemia cells by pharmacological inhibitors of protein kinase C," *Cancer Res.*, 54:1707–1714, 1994.

(List continued on next page.)

*Primary Examiner*—James H. Reamer
(74) *Attorney, Agent, or Firm*—Fulbright & Jaworski LLP

(57) ABSTRACT

Chelerythrine is an effective inhibitor of solid tumor growth and is extremely cytotoxic in combination with chemotherapeutic agents that directly damage DNA.

30 Claims, 6 Drawing Sheets

OTHER PUBLICATIONS

Jung et al., "Mutations in the p53 gene in radiation–sensitive and–resistant human squamous carcinoma cells," *Cancer Res.*, 52:6390–6392, 1992.

Kharbanda et al., "Activation of the c–Abl tyrosine kinase in the stress response to DNA–damaging agents," *Nature*, 376:375–378, 1995.

Nagasawa et al., "Absence of a radiation–induced first–cycle G1–S arrest in p53+ human tumor cells synchronized by mitotic selection," *Cancer Res.*, 58:2036–2041, 1998.

Ramsamooj et al., "Differential expression of proteins in radioresistant and radiosensitive human squamous carcinoma cells," *J. Natl. Cancer Inst.*, 84:622–628, 1992.

Samuels et al., "Increased glutathione peroxidase activity in a human sarcoma cell line with inherent doxorubicin resistance," *Cancer Res.*, 57:521–527, 1991.

Shao et al., "Abrogation of an S–phase checkpoint and potentiation of camptothecin cytotoxicity by 7–hydroxystaurosporine (UCN–01) in human cancer cell lines, possibly influenced by p53 function," *Cancer Res.*, 57:4029–4035, 1997.

U et al., "Mutant p53 may selectively suppress glial specific proteins in pluripotential human neuroectodermal tumor cells," *Neurosci. Lett.*, 244:41–46, 1998.

Vokes and Weichselbaum, "Concomitant Chemoradiotherapy: rationale and clinical experience in patients with solid tumors," *J. Clin. Oncol.*, 8:911–934, 1990.

Vokes et al., "Head and neck cancer,", *N. Eng. J. Med.*, 328:184–194, 1993.

Wang et al., "UNC–01: a Potent Abrogator of G2 Checkpoint Function in Cancer Cells with Disrupted p53," *J. Natural Cancer Inst.*, 88:956–962, 1996.

Chmura et al, Clin. Cance3r Res., vol. 6(2), pp. 737–742 (abstract), 2/2000.*

Dashpande et al, Journal of Cancer Biochemistry, vol. 66, pp. 286–296 (1997).*

* cited by examiner

CHELERYTHRINE-BASED THERAPIES FOR CANCER

The government may own rights in the present invention pursuant to grant numbers GM07183; 5-R01-CA41068; 5-R01-CA42596; P01-CA-19266 and HD-07009 from the National Institutes of Health.

BACKGROUND OF THE INVENTION

1. Field of the Invention

The present invention relates generally to the fields of cancer treatment and chemotherapy. More particularly, it concerns use of the protein kinase C (PKC) inhibitor chelerythrine to treat cancer in combination with DNA damaging chemicals to produce unexpectedly effective killing of tumor cells and tumor endothelial cells.

2. Description of Related Art

Certain cancer treatment methods, including chemotherapeutic therapy, involve damaging the DNA of the cancer cell. The cellular response to normal DNA damage includes activation of DNA repair, cell cycle arrest and lethality (Hall, 1988). For example, the induction of DNA double-strand breaks results in lethal chromosomal aberrations that include deletions, dicentrics, rings, and anaphase bridges (Hall, 1994).

The morphological characteristics of cells dying a mitotic death include, as in necrotic death, multi-nucleated giant cells, cell-cell fusions (Hall, 1994), as well as the loss of membrane integrity (Quintans et al., 1994; Maity et al., 1994; Harmon and Allan, 1988; Radford and Murphy, 1994). In contrast to necrotic death, morphological characteristics of apoptosis (Quintans et al., 1994; Maity et al., 1994; Harmon and Allan, 1988; Radford and Murphy, 1994) include activation of a genetic program that may be initiated by cytoplasmic or nuclear events which results in cytoplasmic blebbing, chromatin condensation, and DNA fragmentation (Jacobson et al., 1994; Raff et al., 1994).

Studies in tumor systems suggest that increasing the fraction of tumor cells undergoing apoptosis enhances tumor regression and tumor cures (Meyn et al., 1993; 1994; 1995; Martin and Green, 1994; Indap and Rao, 1995; Dewey et al., 1995; Lowe et al., 1993b; Stephens et al., 1991; 1993; Chmura et al., 1997). Agents which damage DNA, interfere with DNA repair, or alter cell-cycle checkpoints have been employed in human studies to modify tumor response with limited clinical success (Hall, 1988; Vokes and Weichselbaum, 1990; Rosenthal et al., 1995). Chelerythrine chloride (Herbert et al., 1990) and calphostin C (Kobayashi et al., 1989b), inhibitors of protein kinase C (PKC) isoforms, also induce apoptosis and ceramide production through the activation of a neutral sphingomyelinase (Chmura et al., 1996a; Chmura et al., 1996b). The protein kinase C family of serine/threonine kinases is comprised of at least 13 related isoforms (Magnuson et al., 1994) with differing sensitivity to calcium and lipid activators.

Little information is available concerning the relationship between PKC inhibitors and the induction of programmed cell death in human tumor cells, and the results described in existing reports are inconsistent. For example, the potent, but nonspecific, PKC inhibitor staurosporine has been reported both to antagonize (Cotter et al., 1992) and to initiate apoptosis in HL-60 cells (Bertrand et al., 1993); similarly conflicting reports of the action of the inhibitor H7 have also appeared (Ojeda et al., 1990; Forbes et al., 1992). Detailed comparisons of the concentration-response relationships of different PKC inhibitors in the modulation of apoptosis are generally lacking. Jarvis et al. (1994) demonstrate that, while the effects of these agents are variable and highly dependent upon concentration, transient exposure of HL-60 cells to a subset of PKC inhibitors, in particular chelerythrine, unambiguously induces apoptotic DNA fragmentation and cell death in HL-60 cells, and that acute (i.e., 6 h) exposure to chelerythrine is sufficient to induce apoptosis in the human myeloid leukemia cell line HL-60. In addition, in vitro treatment of certain cells with inhibitors of PKC and other serine-threonine kinases increases IR mediated killing through undefined mechanisms (Hallahan et al., 1992).

Recent investigations indicate that signaling events following cellular exposure to tumor necrosis factor alpha (TNFα), Fas ligand, IgM cross-linking, irradiation and other DNA damaging agents may trigger apoptosis via the hydrolysis of membrane sphingomyelin generating ceramide (Quintans et al., 1994; Nagata and Golstein, 1995; Dressler et al., 1992). Activation of PKC by phorbol esters or growth factors opposes ceramide-induced apoptosis and indirect evidence suggests that PKC activation may limit ceramide production (Fuks et al., 1994; Haimovitz-Friedman et al., 1994a; Haimovitz-Friedman et al., 1994b). In tumor endothelial cells, one potential action of ceramide and its metabolite sphingosine is to prevent activation of specific PKC isoforms (Chmura et al., 1996b; Jones and Murray, 1995; Kolesnick, 1989; Ohta et al., 1994). Taken together, these studies suggest that PKC activation may oppose the actions of ceramide production in the apoptotic pathway in tumor cells and tumor endothelial cells.

Though it is clear that PKC pathways play a key role in the control of apoptosis by tumor cells, how this is accomplished remains obscure. Thus, there remains a present need to develop new and improved treatments which take advantage of these pathways.

SUMMARY OF THE INVENTION

The invention provides a method for inhibiting growth of a tumor cell comprising contacting the tumor cell and/or the tumor endothelial cell with chelerythrine and contacting the tumor cell with DNA damaging agent, wherein the dose of the chelerythrine, when combined with the dose of the DNA damaging agent, is effective to inhibit growth of the tumor cell.

The invention further provides a method for inhibiting the growth of a cell comprising contacting the cell with chelerythrine and a chemotherapeutic DNA damaging agent, wherein the dose of chelerythrine, when combined with the dose of the DNA damaging agent, is effective to inhibit growth of the cell. In one embodiment of the method, chelerythrine is contacted with the cell prior to contacting the cell with the DNA damaging agent. In another embodiment of the method, the DNA damaging agent is contacted with the cell prior to contacting the cell with chelerythrine.

In a further embodiment of the method, the cell is a cancer cell. In a further aspect of the invention, the cancer cell is a bladder cancer cell, a blood cancer, a breast cancer cell, a lung cancer cell, a colon cancer cell, a prostate cancer cell, a liver cancer cell, a pancreatic cancer cell, a stomach cancer cell, a testicular cancer cell, a brain cancer cell, an ovarian cancer cell, a lymphatic cancer cell, a skin cancer cell, a brain cancer cell, a bone cancer cell, or tumor of soft tissue. In yet another aspect of the invention, the cell is located in a human subject.

In one embodiment of the invention, chelerythrine is administered by direct intratumoral injection. In another embodiment of the invention, chelerythrine is administered by injection into tumor vasculature. In a further embodiment of the invention, the DNA damaging agent is from a group consisting of doxorubicin, daunorubicin, dactinomycin, mitoxantrone, cisplatin, procarbazine, mitomycin, carboplatin, bleomycin, etoposide, teniposide, mechlroethamine, cyclophosphamide, ifosfamide, melphalan, chlorambucil, ifosfamide, melphalan, hexamethylmelamine, thiopeta, busulfan, carmustine, lomustine, semustine, streptozocin, dacarbazine, adriamycin, 5-fluorouracil (5FU), camptothecin, actinomycin-D, hydrogen peroxide, nitrosurea, plicomycin, tamoxifen, taxol, transplatinum, vincristin, vinblastin and methotrexate.

In one aspect of the invention, the cell is contacted with chelerythrine a second time. In another aspect of the invention, the cell is contacted with the DNA damaging agent a second time. In one embodiment of the invention, chelerythrine and the DNA damaging agent are contacted with the cell within about 4 days. In another embodiment of the invention, chelerythrine and the DNA damaging agent are contacted with the cell within about 3 days. In yet another embodiment of the invention, chelerythrine and the DNA damaging agent are contacted with the cell within about 2 days. In still another embodiment of the invention, chelerythrine and the DNA damaging agent are contacted with the cell within about 1 day. In still yet another embodiment of the invention, chelerythrine and the DNA damaging agent are contacted with the cell within about 12 hours. In still another embodiment of the invention, chelerythrine and the DNA damaging agent are contacted with the cell within about 6 hours. In yet another embodiment of the invention, chelerythrine and the DNA damaging agent are contacted with the cell within about 5 hours. In still other embodiment of the invention, chelerythrine and the DNA damaging agent are contacted with the cell within about 4 hours. In yet other embodiments of the invention, chelerythrine and the DNA damaging agent are contacted with the cell within about 3 hours. In still another embodiment of the invention, chelerythrine and the DNA damaging agent are contacted with the cell within about 2 hours. In another embodiment of the invention, chelerythrine and the DNA damaging agent are contacted with the cell within about 1 hour. In a further embodiment of the invention, chelerythrine and the DNA damaging agent are contacted with the cell at the same time. Thus, in various embodiments of the invention, chelerythrine and the DNA damaging agent are contacted with the cell within about 4 days, 3 days, 2 days, 1 day, 12 hours, 6 hours, 5.5 hours, 5 hours, 4.5 hours, 4 hours, 3.5 hours, 3 hours, 2.5 hours, 2 hours, 1.5 hours, 1 hour, 0.5 hour or at the same time.

In one aspect of the invention, the chelerythrine and the DNA damaging agent are contacted with the cell following tumor resection. In one embodiment of the invention, the tumor resection occurs prior to the contacting. In one aspect of the invention, the contacting comprises treating the resected tumor bed with chelerythrine and the DNA damaging agent. In another embodiment of the invention the tumor resection occurs after the contacting. In a further embodiment of the invention, the contacting occurs both before and after the tumor resection.

In one embodiment of the invention, the dose of chelerythrine is about 0.5 mg/kg to about 10 mg/kg. In another embodiment of the invention, the dose of chelerythrine is about 1 mg/kg to about 4 mg/kg. However, one of skill in the art will recognize that the dose of chelerythrine administered will depend on the animal or human being treated and will be decided by factors such as, but not limited to, the age and weight of animal or patient and may vary by a log or more of the values described above. The skilled artisan is directed to "Remington's Pharmaceutical Sciences" 15th Edition, chapter 33, in particular pages 624–652. The skilled artisan will further recognize that some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The invention further provides a method of killing a cell comprising contacting the tumor cell with chelerythrine and a chemotherapeutic DNA damaging agent, wherein the dose of the chelerythrine, when combined with the dose of the DNA damaging agent, is effective to kill the tumor cell. In one embodiment of the invention, a method of treating cancer in a human patient comprising administering chelerythrine and a chemotherapeutic DNA damaging agent to the human patient, wherein the dose of the chelerythrine, when combined with the dose of the DNA damaging agent, is effective to treat the cancer. In a further embodiment of the invention, a method of potentiating the effect of a chemotherapeutic DNA damaging agent on a tumor cell and/or a tumor endothelial cell comprising contacting the tumor cell and/or a tumor endothelial cell with chelerythrine and then contacting the tumor cell and/or a tumor endothelial cell with the DNA damaging agent.

As defined herein, treatment of a cancer, tumor, tumor cell, tumor endothelial cell, cancer cell, tissue derived from a tumor or cancerous tissue refers to any improvement over the untreated state which includes, but is not limited to, stabilization, remission, regression, shrinkage or decreased volume of the cancer, tumor, tissue or cell.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2A depicts that MCF7 (closed circle), MCF7ADR (open circle), HT29 (open square), DAOY (closed triangle) and LnCaP (open triangle) cells were exposed to fresh medium containing increasing concentrations of chelerythrine chloride for 4 h. After 6 days (MCF7, MCF7 ADR, HT29), 7 days (DAOY) or 13 days (LnCAP), MTT analysis was performed to determine cell density. Inhibition of cell growth relative to control (zero drug addition) was calculated for each concentration. Each point represents the mean of three determinations. FIG. 2B depicts that SQ20B (closed circle), JSQ3 (open circle), SCC35 (closed square) and SCC61 (open square) cells were exposed to fresh medium containing increasing concentrations of chelerythrine chloride for 4 h. After 6 days (SQ20B), 12 days (JSQ3, SCC35) or 13 days (SCC61), MTT analysis was performed to determine cell density. Inhibition of cell growth relative to control (zero drug addition) was calculated for each concentration. Each point represents the mean of three determinations.

FIG. 3A shows that cells treated with 5 µM chelerythrine appear apoptotic with condensed nuclei and chromatin condensation 12 h after addition of drug to exponentially growing SQ-20B cells. DAPI was used to visualize nuclei (red) and overlaid to the phase contrast image. Left, untreated control cells, right 5 µM chelerythrine treated cells.

FIG. 3B shows that analysis of low molecular weight DNA by agarose electrophoresis (3%) isolated from $5 \times 10^6$ SQ-20B cells demonstrating characteristic laddering 12 h following exposure to 5 µM chelerythrine. (−) control; (CH) chelerythrine FIG. 4. Chelerythrine induces growth delay.

Athymic (nude) mice were injected SC in the right hind limb with $5 \times 10^6$ SQ20B cells. Tumors were allowed to grow for 8 days at which time treatment was started. Control mice were weighed and injected IP with PBS on days 8, 10, and 12. Treatment group 2 (n=10 were injected once IP on days 8, 10, and 12 with 2.5 mg/kg chelerythrine chloride, treatment group 3 (n=8) were injected once IP on days 8, 10, and 12 with 5 mg/kg chelerythrine chloride, and treatment group 4 (n=8) were injected once IP on days 8, 11 and 14 with 5 mg/kg chelerythrine chloride. Tumor volume was determined on days 8, 10, 13, 15, 17, 21. Each data point represents the mean of 1–3 individual studies +/−SEM. The Mann-Whitney Rank Sum Test (p<0.05) denoted in the graphs by "*".

Figure 5:
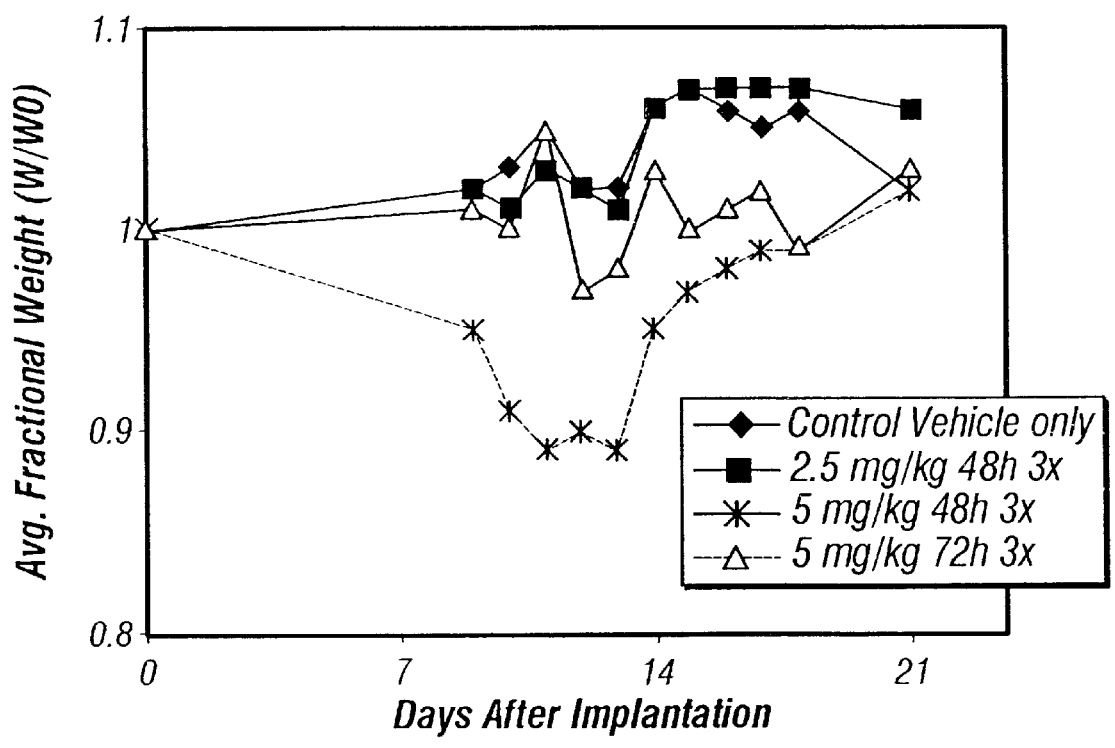

FIG. 5. Effect of treatment with chelerythrine on body weight.

Mice were weighed on days 8, 9, 10, 11, 12, 13, 14, 15, 16, 17, 18, 21. Symbols represent the mean weight of animals in the representative treatment groups.

Figure 6:
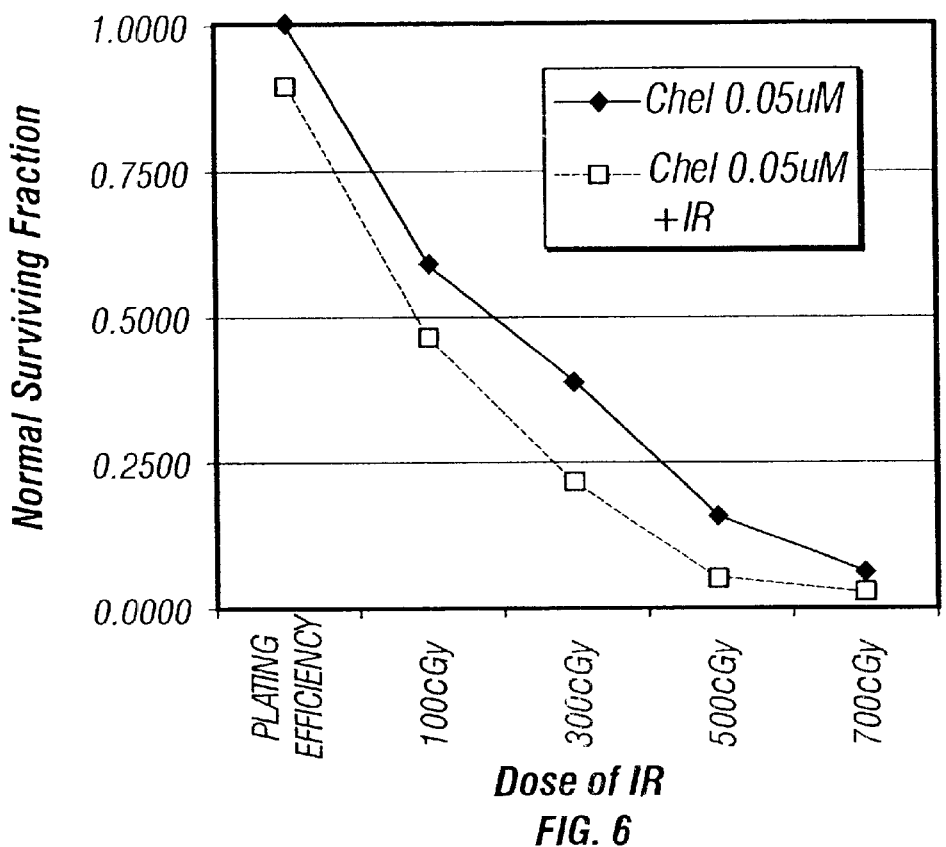

FIG. 6. Chelerythrine chloride enhances IR induced cell killing in endothelial cells in vitro.

This FIG. demonstrates that the proliferation endothelial cells, comprising the tumor vasculature bed, are more sensitive to chelerythrine, both in terms of apoptosis and in terms of clonogenic killing. Thus, part of the in vivo mechanism of killing is a result of targeting the tumor vasculature.

Figure 7:
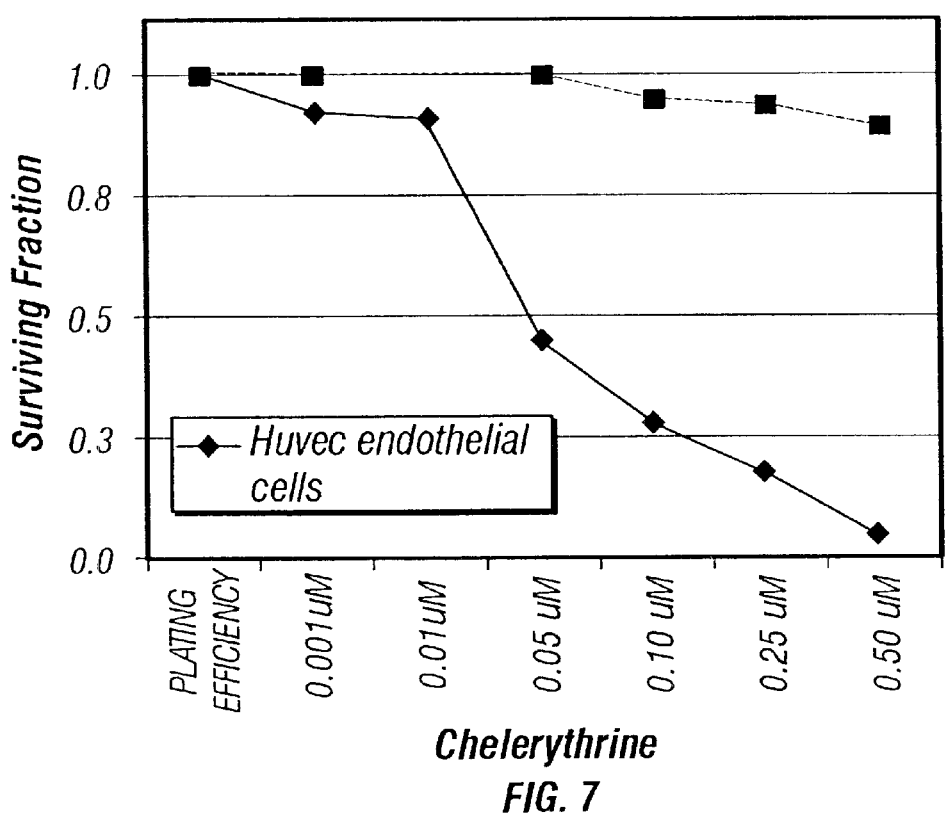

FIG. 7. Endothelial cells are more sensitive to clonogenic killing by chelerythrine compared to tumor cells such as SQ-20B.

Figure 8:
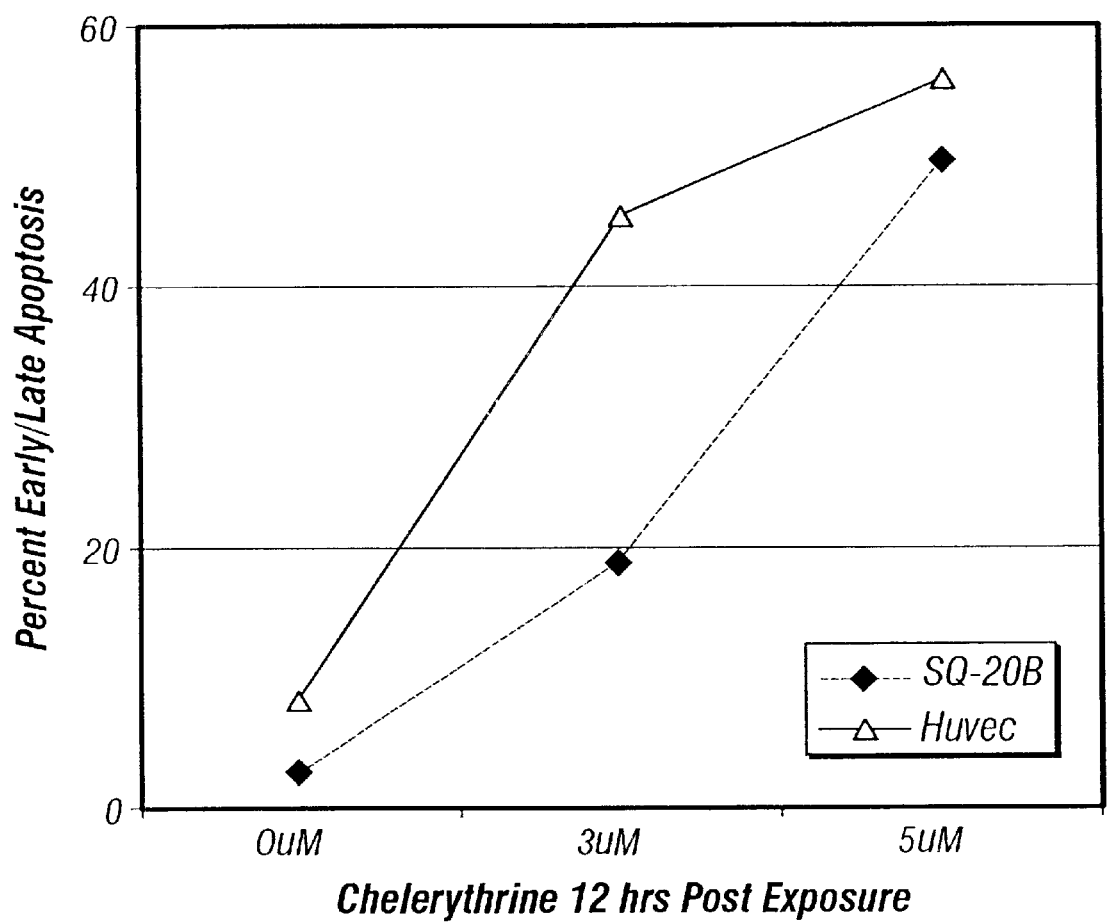

FIG. 8. Endothelial cells are more sensitive to chelerythrine induced apoptosis as compared to tumor cells such as SQ-20B.

DESCRIPTION OF ILLUSTRATIVE EMBODIMENTS

The present invention demonstrates that chelerythrine chloride inhibits tumor cell growth and or induces cell death in certain tumor cells in combination with a chemotherapeutic compound. In addition, the induction of apoptosis by a combination of chelerythrine and a chemical DNA damaging agent permits effective treatment occurs at doses much lower than use of either agent alone.

The combination treatment of tumor cells and/or a tumor endothelial cells with DNA damaging agents and chelerythrine increases apoptosis. Chelerythrine chloride enhances chemotherapy-induced apoptosis by targeting common components of the cell death pathway required for apoptosis and overcome resistance to chemotherapy-induced apoptosis in vitro and in vivo.

The present invention demonstrates an increase in tumor cell destruction compared to surrounding normal tissue and indicates that chelerythrine when combined with DNA damaging chemotherapy, is a clinically useful tool for enhancing the lethal effects of ionizing radiation in resistant tumor cell populations.

A. Chelerythrine as an Inhibitor of Tumor Growth

Protein kinase C (PKC) isoenzymes are involved in the regulation of cell proliferation, differentiation, and survival. Pharmacological inhibition of PKC activity triggers apoptosis in most mammalian cells. While PKC inhibitors have potential as anti-tumor agents, issues of kinase specificity and solubility have remained obstacles to their clinical use. In this invention, the inventors investigated the anti-tumor activity of the PKC inhibitor chelerythrine chloride (chelerythrine), a selective inhibitor of group A and B PKC isoforms. Chelerythrine exhibited cytotoxic activity against 9 human tumor cell lines tested in vitro. Based on the finding that radioresistant and chemoresistant squamous cell carcinoma lines (HNSCC) are sensitive to chelerythrine in vitro, the inventors assessed the effects of this agent on p53 deficient SQ-20B HNSCC cells in vivo. The results demonstrate that chelerythrine treatment of nude mice bearing SQ-20B is associated with significant tumor growth delay and regression. Significantly, treatment with chelerythrine resulted in minimal toxicity. These findings demonstrate that chelerythrine has anti-tumor activity.

B. Protein Kinase C and Chelerythrine

Protein kinase C (PKC) isozymes comprise a family of at least 11 serine/threonine protein kinases. All PKC family members contain an amino-terminal regulatory domain that includes pbosphatidylserine (PS) and phorbol ester binding sites (Bell and Burns, 1991). The carboxyl-terminal catalytic domain binds both ATP and substrate, and contains autophosphorylation sites. The carboxyl-terminal domain represents a main target for pharmacological inhibition of PKC isoforns.

Non-specific inhibitors of serine-threonine kinases, such as the fungal alkaloid staurosporine, have been used to study the role of PKC inhibition in the induction of apoptosis. The results demonstrate that kinase inhibition triggers apoptosis of nucleated mammalian cells throughout different phases of the cell cycle (Raff et al., 1994; Jacobson et al., 1994; Weil et al., 1996; Jacobsen et al., 1996). Apoptosis also is induced following cellular exposure to other PKC inhibitors, such as naphthalene sulfonamides (H7 and H8) (Jarvis et al., 1994; McConkey et al., 1989) and the ceramide metabolite sphingosine (Schwartz et al., 1995; Gottschalk and Quintans, 1995; Ohta et al., 1994; Hannun and Lindardic, 1993; Jarvis et al., 1996). Significantly, numerous reports have demonstrated little if any selectivity of these inhibitors for PKC as compared to other intracellular kinases (Birchall et al., 1994, Bradshaw et al., 1993). Therefore, the role of PKC inhibition as a major effector of apoptosis has remained unclear.

In the induction of apoptosis, several intracellular events are altered prior to the activation of caspases. These events include release of free $Ca^{2+}$ from intracellular stores, down-regulation of Bcl-2, (Knox et al, 1993; Shirahama et al., 1997; May et al., 1994), and $p34^{cdc2}$ activation outside of the G2/M cell cycle phase (Donaldson et al., 1994; Shi et al., 1994; Schroter et al., 1996; Osmani et al., 1991). PKC activity is important in suppressing sphingomyelin hydrolysis and the subsequent induction of apoptosis by ceramide (Haimovitz-Friedman et al., 1994, Gottschalk et al., 1995). In this context, inhibition of PKC with chelerythrine chloride induces apoptosis by activation of a neutral sphingomyelinase, accumulation of ceramide and depletion of sphingomyelin (Jarvis et al., 1996; Chmura et al., 1996a; Chmura et al., 1996b; Grant et al., 1994). These findings suggest that PKC inhibition also may trigger apoptosis through the activation of the ceramide-signaling cascade.

Derivatives of staurosporine have been isolated in an attempt to obtain more specific inhibition of PKC. One of the most specific PKC inhibitors, developed is chelerythrine chloride (Herbert et al., 1990), a benzophenanthridine alkaloid. In contrast to staurosporine, chelerythrine is at least 100-fold more selective for PKCs than for other kinases (i.e., PKA, PKG). Chelerythrine competes for the conserved catalytic sites of PKC and append to be a potent and specific inhibitor of the group A and group B kinases (29–32). Unlike H7 and staurosporine, chelerythrine does not inhibit other kinases or activate phospholipase D (PLD) at concentrations that induce apoptosis. The specificity of chelerythrine for PKC has prompted the use of this agent to study PKC function in cells (Gupta et al., 1995).

The inventors report herein that chelerythrine chloride (chelerythrine) is cytotoxic to 9 human tumor cell lines and tumor endothelial cells. Chelerythrine was chosen for its kinase specificity, ease of delivery in vivo, ability to trigger ceramide accumulation, and inhibition of PKC in an ATP-independent manner (Herbert et al., 1990; Rotenberg et al., 1995; Nixon et al., 1992). The inventors selected a p53-deficient chemo/radiation resistant tumor cell heel SQ-20B, to test whether chelerythrine induces growth delay or tumor regression in vivo. The inventors identify apoptosis as the main mechanism of chelerythrine-induced cell killing in vitro. Treatment of nude mice bearing SQ-20B xenograft tumors with IP chelerythrine produced growth delay and tumor regression. Importantly, chelerythrine exhibited little if any systemic toxicity. The pre-clinical findings suggest that chelerythrine could be effective in the treatment of human tumors that are otherwise resistant to standard regimens.

C. Combination of Low Doses of Chelerythrine and DNA Damaging Agents

Tumor cell resistance to DNA damaging agents represents a major problem in clinical oncology. One goal of current cancer research is to find ways to improve the efficacy of chemotherapy. In the context of the present invention, it is contemplated that combination of therapy with chelerythrine or chelerythrine chloride, with DNA damaging chemotherapy can be employed advantageously in a therapeutic intervention. One result of the present invention is that the combination of chelerythrine and DNA damaging agents allows for the use of lower doses of each composition in order to achieve a higher level of tumor growth reduction than would be predicted based upon current conventional chemotherapies. For example, in combination therapy of chelerythrine with adriamycin, 2 $\mu$M chelerythrine and 10 g/ml of adriamycin has only 0.668 survival as compared to 0.99 survival with 2 $\mu$M chelerythrine alone or 0.822 with 10 ng/ml of adriamycin alone (see Table 1). Thus, toxic and other adverse effects which chemotherapy causes to healthy cells that must be exposed to the these drugs during treatment can be reduced by using the present invention.

Herein, it is understood that treatment with chelerythrine is preferentially with chelerythrine chloride. To inhibit or even kill cells, such as malignant or metastatic cells, using the methods and compositions of the present invention, one would generally contact a "target" cell with chelerythrine and a DNA damaging agent. These compositions would be provided in a combined amount effective to inhibit proliferation, or restore apoptotic function or even kill the cell. This process may involve contacting the cells with chelerythrine and the DNA damaging agent simultaneously, or with chelerythrine followed by the DNA damaging agent, or with the DNA damaging agent followed by chelerythrine. The cells may be contacted with a single composition or pharmacological formulation of chelerythrine and the DNA damaging agent, or with two distinct compositions or formulations, one comprising chelerythrine and the other comprising the DNA damaging agent.

It is envisioned that the regional delivery of chelerythrine and DNA damaging agents to patients with cancers will be a very efficient method for delivering a therapeutically effective amount of the compound to counteract the clinical disease. A local administration also is useful, and includes direct injection of tumor mass, circumferential injection, and injections or bathing of a resected tumor bed. Alternatively, systemic delivery of either chelerythrine, DNA damaging agents, or both is appropriate in certain circumstances, for example, where extensive metastasis has occurred.

D. Chelerythrine, a Benzophenanthridine Alkaloid

The benzophenanthridine alkaloid chelerythrine (1,2-dimethoxy- 12-methyl[1,3]benzodioxolo[5,6-c] phenanthridinium; $C_{21}H_{18}NO_4$), also known as toddaline, is extractable either in pure form or as a mixture with other benzophenanthridine alkaloids from *Chelidonium majus* L., *Zanthoxylum simulans*, *Sanguinaria candensis* (or bloodroot), *Macleaya cordata*, *Carydali sevctocozii*, *Carydali ledebouni*, *Chelidonium majusm* and other members of Papaveracaceae. The major alkaloid in *Zanthoxylum simulans*, is chelerythrine with smaller quantities of dihydro- and oxy-chelerythrine, N-acetylanomine, skimmianine, fagarine, sitosterol and sesamine. Gray et al., (1980) describes the extraction and identification of chelerythrine and other constituents from *Zanthoxylum simulans*.

Other benzo-c-phenanthridine alkaloids which may be present in the plants with chelerythrine include sanguinarine, sanguirubine, sanguilutine, homochelidonene, chelirubine and protopine among others. Pure chelerythrine is also available, although rarely, from some chemical supply houses. Semi-purified forms of benzo-c-phenanthridine alkaloids are commercially available, and these are generally referred to as sanguinarine nitrate and sanguinarine sulfate. These "salts" are the salts of the mixed alkaloids of the plant Sanguinaria and mainly comprise sanguinarine, chelerythrine, and protopine.

While few references can be found in the literature regarding the usage of any of the pure benzo-c-phenanthridine alkaloids, plants containing such compounds have been used for medical purposes for quite some time for a wide variety of ailments. For example, U.S. Pat. No. 209,331, discloses the use of bloodroot, zinc chloride, and kerosene oil in equal proportions for treating open sores. U.S. Pat. No. 433,257 describes a salve of pulverized bloodroot, armenian bole, powdered rosin, lard, and Stockholm tar for use in the treatment of piles, and U.S. Pat. No. 2,344,830, discloses the use of a mixture of zinc chloride, stibnite, and bloodroot, to fix and outline diseased tissue for excision by surgery. Some of the patents describing the use of sanguinaria extracts as antimicrobial agents are U.S. Pat. Nos. 4,145,412; 4,406,881; and 4,376,115. Chelerythrine has also been used for the treatment of peridontal disease, U.S. Pat. No. 5,324,520, and in the treatment of thrombosis, U.S. Pat. No. 5,137,912. Benzo-c-phenanthridine alkaloids have also been shown to have some antifungal and antiprotozoan properties, alleviate the mild anemia lingering after an acute illness and the mild anemia associated with rheumatoid arthritis.

In China, people use the berries of *Zanthoxylum simulans* to flavor pork. The long and widespread use of this extract in China shows that the extract is safe for human consumption. The extract has an absence of any noticeable side effects and lack of irritation to the gastrointestinal tract. Moreover, the extract has been found to help alleviate the gastrointestinal irritations which may occur through the use of the anti-inflammatory agents when coadministered.

Figure 1:
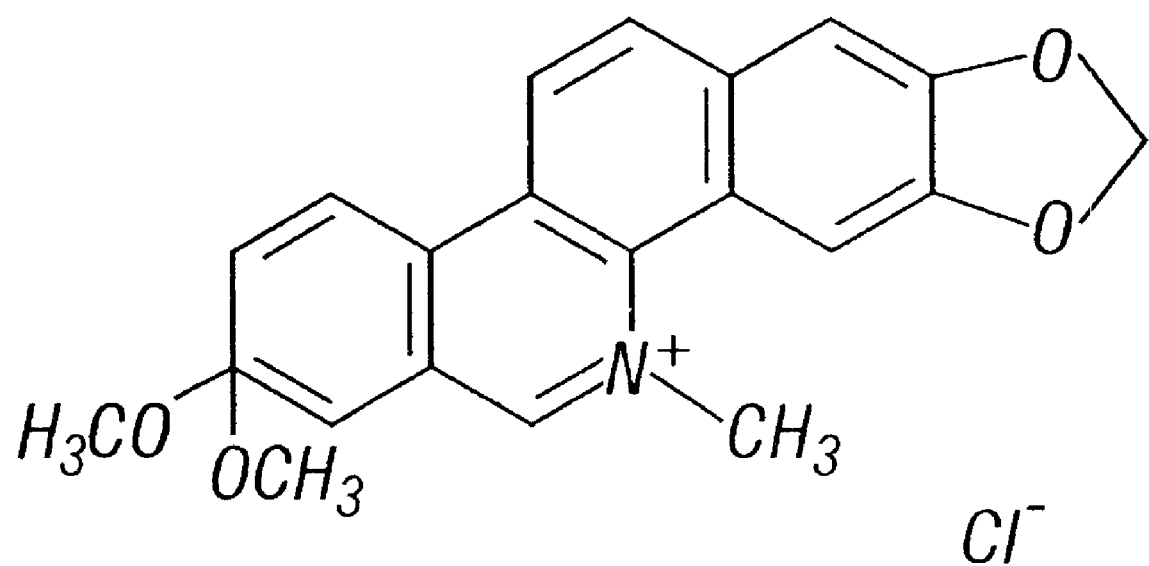
FIG. 1. Chemical structure of cheleryihrine

Chelerythrine specifically inhibits protein kinase C (PKC) in a concentration-dependent manner and strongly inhibits platelet aggregation induced by strong aggregation inducers, such as arachidonic acid and collagen. Its chemical structure is shown in FIG. 1.

Inhibitors of PKC can interact with the substrate binding site (ATP or protein) or with the regulatory domain where activation occurs (diacylglycerol or phorbol ester binding site). Chelerythrine interacts directing with the catalytic domain of PKC. It is one of the most potent inhibitors of PKC identified and does not inhibit any other protein kinases investigated. Chelerythrine shows potent cytotoxic effects against L-1210 tumor cells with an IC50 value of 0.053 $\mu$M by inhibiting cell growth and differentiation (Herbert et al., 1990).

Chelerythrine exhibits biphasic concentration-response relationships such that DNA fragmentation declines and eventually subsides as drug levels are increased beyond maximally effective concentrations (Jarvis et al, 1994). Reductions in DNA damage are not associated with restoration of cellular viability, however, indicating that other lethal events proceeded unimpaired.

Under the conditions described by Herbert et al. (1990) the $IC_{50}$ value (concentration causing a 50% inhibition) for chelerythrine is 0.66 $\mu$M in rats. Basal activity of the enzyme (the activity in the absence of $Ca^{++}$, phosphatidylserine and dioleine) was not affected. In the present invention, the $LD_{50}$ (dose causing a 50% mortality) was 20 mg/kg intraperitoneal (IP) in mice.

An effective dose of chelerythrine is highly dependent upon the route of administration used and the size and species of animal being treated. In general, orally delivered doses can be higher than injected doses for any given individual. In the present invention, an effective dose is a dose that can induce apoptosis in a treated cell. Particularly desirable cells to treat include tumor and cancer cells and especially radio-resistant tumor or cancer cells. An exemplary effective dose range is equivalent to about 0.5–10 mg/kg (IP) in a mouse and more preferably 1–4 mg/kg (IP) in a mouse.

E. DNA Damaging Chemicals

A variety of chemical compounds, also described as "chemotherapeutic agents", function to induce DNA damage, are used to treat tumors. Chemotherapeutic agents contemplated to be of use, include, doxorubicin, daunorubicin, dactinomycin, mitoxantrone, cisplatin (CDDP), procarbazine, mitomycin, carboplatin, bleomycin, etoposide (VP-16), teniposide, mechlroethamine, cyclophosphamide, ifosfamide, melphalan, chlorambucil, ifosfamide, melphalan, hexamethylmelamine, thiopeta, busulfan, carmustine, lomustine, semustine, streptozocin, dacarbazine, adriamycin, 5-fluorouracil (5FU), camptothecin, actinomycin-D, hydrogen peroxide , nitrosurea, plicomycin, tamoxifen, taxol, transplatinum, vincristin, vinblastin and methotrexate to mention a few.

Agents that damage DNA include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25–75 $mg/m^2$ at 21 day intervals for adriamycin, to 35–50 $mg/m^2$ for etoposide intravenously or double the intravenous dose orally.

Agents that disrupt the synthesis and fidelity of nucleic acid precursors and subunits also lead to DNA damage. A number of such agents have been developed, particularly useful are agents that have undergone extensive testing and are readily available. 5-fluorouracil (5-FU), is one such agent that is preferentially used by neoplastic tissue, making it particularly useful for targeting neoplastic cells. Thus, although quite toxic, 5-FU, is applicable with a wide range of carriers, including topical and even intravenous administrations with doses ranging from 3 to 15 mg/kg/day.

Agents that directly cross-link nucleic acids, specifically DNA, are envisaged to facilitate DNA damage leading to a useful antineoplastic treatment. For example, cisplatin, and other DNA alkylating agents may be used. Cisplatin has been widely used to treat cancer, with efficacious doses used in clinical applications of 20 $mg/m^2$ for 5 days every three weeks for a total of three courses. Cisplatin is not absorbed orally and must therefore be delivered via injection intravenously, subcutaneously, intratumorally or intraperitoneally.

F. Adjunct Therapies (i) Radiotherapeutic Agents

Radiotherapeutic agents and factors include radiation and waves that induce DNA damage for example, $\gamma$-irradiation, X-rays, UV-irradiation, microwaves, electronic emissions, radioisotopes, and the like. Therapy may be achieved by irradiating the localized tumor site with the above described forms of radiations. It is most likely that all of these factors effect a broad range of damage DNA, on the precursors of DNA, the replication and repair of DNA, and the assembly and maintenance of chromosomes.

Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

(ii) Surgery

Surgical treatment for removal of the cancerous growth is generally a standard procedure for the treatment of tumors and cancers. This attempts to remove the entire cancerous growth. However, surgery is generally combined with chemothrapy and/or radiotherapy to ensure the destruction of any remaining neoplastic or malignant cells. Thus, surgery may be used in combination with the present invention.

G. Therapeutic Regimens

Tumors that can be treated with the present invention include, but are not limited to, tumors of the brain (glioblastomas, medulloblastoma, astrocytoma, oligodendroglioma, ependymomas), lung, liver, spleen, kidney, lymph node, small intestine, pancreas, blood cells, colon, stomach, breast, endometrium, prostate, testicle, ovary, skin, head and neck, esophagus, bone marrow, blood or other tissue. The tumor may be distinguished as metastatic and non-metastatic. Various embodiments include tumor cells of the skin, muscle, facia, brain, prostate, breast, endometrium, lung, head & neck, pancreas, small intestine, blood cells, liver, testes, ovaries, colon, skin, stomach, esophagus, spleen, lymph node, bone marrow or kidney. Other embodiments include fluid samples such as peripheral blood, lymph fluid, ascites, serous fluid, pleural effusion, sputum, cerebrospinal fluid, lacrimal fluid, stool or urine.

"Effective amount" is defined as an amount of the agent that will decrease, reduce, inhibit or otherwise abrogate the growth of a cancer cell, induce apoptosis, inhibit metastasis, kill cells or induce cytotoxicity in cells.

Combination treatments with chelerythrine may precede or follow the DNA damaging chemotherapy by intervals ranging from seconds to weeks. In embodiments where chelerythrine and the DNA damaging agent are applied separately to the cell, one would generally ensure that a significant period of time did not expire between the time of each delivery, such that the combination of the two would still be able to exert an advantageously combined effect on the cell. In such instances, it is contemplated that one would contact the cell with both agents within about 0.1 to 24 hours of each other and, more preferably, within about 1 to 4 hours of each other, with a delay time of only about 1 hour to about 2 hours being most preferred. In some situations, it is desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either chelerythrine or the DNA damaging agent will be desired. Various combinations may be employed, where chelerythrine is "A" and the DNA damaging agent is "B":

| | | | | |
|---|---|---|---|---|
| A/B/B | B/A/A | A/A/B | | |
| A/B/A | B/A/B | B/B/A | | |
| B/B/B/A | B/B/A/B | B/A/B/A | B/A/A/B | |
| A/A/B/B | A/B/A/B | A/B/B/A | | |
| A/A/A/B | B/A/A/A | A/B/A/A | B/B/A/A | |
| B/A/B/B | A/A/B/A | A/B/B/B | | |

To achieve cell killing, both agents are delivered to a cell in a combined amount effective to kill the cell.

H. Treatment Routes

Chelerythrine can be administered intravenously, intraarterially, intratumorally, parenterally or intraperitoneally. In the invention, the preferred routes of administration are directly intratumoral, injection of a resected tumor bed, local or regional administration to the tumor by intravenous (IV); intrarterial (IA); and intraperitoneal (IP) methods. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

Chelerythrine may also be orally administered, for example, with an inert diluent or with an assimilable edible carrier, or enclosed in hard or soft shell gelatin capsule, or compressed into tablets, or incorporated directly with the food of the diet. For oral therapeutic administration, the active compound may be incorporated with excipients and used in the form of ingestible tablets, buccal tables, troches, capsules, elixirs, suspensions, syrups, wafers, and the like. Such compositions and preparations should contain at least 0.1% of the active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

I. Screening and Monitoring Effectiveness of Therapy

It is contemplated that in the context of the present invention one may remove cells, either tumor, normal or both tumor and normal cells, from an individual in order to either monitor the progress of treatment or as a part of the treatment. It is expected that one may monitor the effectiveness of treatment by removing such cells and treating such cells with DAPI staining to determine the level of chromatin condensation, measuring the level of apoptosis, measuring the level of neutral sphingomyelinase production or other methods such as the following.

One particular method for determining induction of apoptosis is terminal deoxynucleotidyl transferase mediated dUTP-biotin nick end labeling (TUNEL) assays, which measure the integrity of DNA (Gorczyca, 1993). This assay measures the fragmentation of DNA by monitoring the incorporation of labeled UTP into broken DNA strands by the enzyme terminal transferase. The incorporation can be monitored by electroscopy or by cell sorting methodologies (e.g., FACS).

J. Ex vivo Delivery

In the present invention, it is contemplated that systemic delivery of either or both chelerythrine and the DNA-damaging agent may be used. It is further contemplated that in practicing the claimed invention that one will wish to replace affected cells with healthy cells from the same patient. Ex vivo gene therapy refers to the isolation of cells from an animal or patient, the delivery of a nucleic acid into the cells in vitro, and then the return of the modified cells back into an animal or individual. This may involve the surgical removal of tissue/organs from an animal or patient or the primary culture of cells and tissues.

In particular, autologous bone marrow cell (BMC) transplantation is used as a salvage procedure in which blood or bone marrow is taken and stored prior to an intensification of radiation or chemotherapy. In preparing human mononuclear cells (MNC), an aliquot of marrow is layered into a receptacle such as a centrifuge tube. Initially, MNC may be obtained from a source of bone marrow, e.g., tibiae, femora, spine, ribs, hips, sternum, as well as the humeri, radi, ulna, tibiae, and fibulae. Additionally, these cells also can be obtained from cord blood, peripheral blood, or cytokine-mobilized peripheral blood. Other sources of human hematopoietic stem cells include embryonic yolk sac, fetal liver, fetal and adult spleen, and blood. The marrow layer is centrifuged to produce a pellet of red cells at the bottom of the tube, a clear layer of media, an interface layer which contains the MNC and a plasma medium layer on top. The interface layer may then be removed using, for example, suction. Centrifugation of this layer at 1000 g ultimately yields a MNC pellet. This pellet may then be resuspended in a suitable buffer for cell sorting by FACS. The isolated MNC are cloned in vitro to expand the of immunologically active cells. The expanded, therapeutically active cells are then provided to the patient to obtain a therapeutic effect.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Drugs and Reagents

Chelerythrine [$IC_{50}$ (PKC)=0.66 $\mu$M, $IC_{50}$ (PKA)=170 $\mu$M] and Calphostin C [$IC_{50}$ (PKC)=0.50 nM, $IC_{50}$ (PKA) 50 $\mu$M] show high specificity for the PKC family of enzymes (Sigma). These inhibitors are at least 30 fold more specific at blocking PKC activity as opposed to the relatively non-selective yet widely used agents staurosporin and H7. They do not appear to inhibit other kinases such as the cyclic-AMP kinase (PKA) at concentrations used for the inventors' studies. (Kobayashi et al., 1989b; Herbert et al., 1990). Chelerythrine chloride, 7-amino-actinomycin D, ATP, phosphate buffered saline (PBS), sphingosine-1-phosphate, DL-threo-dihydrosphingosine and propidium iodide were purchased from Sigma Chemical Corp., St. Louis, Mo. C2-ceramide and n-oleoylethanolamine were purchased from Matreya Chemicals, Pa. Reagents for the terminal transferase assay were purchased from Boehringer-Mannheim Biochemicals, Indianapolis, Ind. Thin-layer chromatography plates were purchased from Whatman (10 cm×10 cm LHP-K TLC plate). Autoradiography film was from Dupont. [$^3$H] palmitic acid (60 Ci/mmol), [$^{14}$C] sphingomyelin (60 Ci/mmol), and [$\gamma$-$^{32}$P] ATP were purchased from DuPont NEN. All solvents were HPLC grade. Chelerythrine was dissolved in sterile water for the in vitro experiments or PBS for the intratumoral injections.

Cell Culture

Human head and neck squamous cell carcinoma line (SQ-20B) was grown in DMEM:F-12 (3:1), 20% fetal bovine serum (Gibco/BRL, Grand Island, N.Y.), 1% penicillin-streptomycin and 1% hydrocortisone at 37° C. in a humidified atmosphere containing 5% $CO_2$. The human colon carcinoma cell line HT29 was obtained from Dr. L. C. Erickson, Loyola Medical Center, Maywood, Ill., and was grown in Dulbecco's Modified Eagle's medium supplemented with 10% fetal bovine serum and 2 mM L-glutamine. MCF7 cells resistant to adriamycin (MCF7 ADR) originated in Dr. K. Cowan's laboratory (NCI, Bethesda, Md.). All MCF7 cells were grown in Richter's Improved Modified Eagle's medium supplemented with 10% fetal bovine serum and 2.2 g/L sodium bicarbonate. DaOY cells were grown in Richters Improved MEM Zinc Option Medium supplemented with 10% fetal bovine serum, 2.2 g/L sodium bicarbonate, 40 $\mu$g/ml Gentamycin, 20 mM HEPES and 10 mM L-glutamine. SQ20B, SCC61, JSQ3 and SCC35 were grown in 75% Dulbecco's Modified Eagle's medium, 25% Ham's F-12K medium supplemented with 20% fetal bovine serum, 0.4 $\mu$g/ml hydrocortisone and 100 units/ml penicillin-streptomycin. All cell cultures were maintained at 37° C. in 5% $CO_2$/95% humidified air.

Cytotoxicity Assay

Cytotoxicity was evaluated using modifications of a described MTT assay (Hansen et al., 1989). Briefly, cells growing as a monolayer were plated at a density of 500 cells/well in 96 well-plates and allowed to grow for 24 h. Following a 4 h incubation with drug, the drug-containing media was replaced win fresh media. 6–13 days after drug treatment, 25 $\mu$l of a 5 mg/ml solution of MTT was added to each well followed 4 h later by the addition of 100 $\mu$l lysing buffer (20% sodium dodecyl sulfate, 50% N, N-dimethylformamide and 0.8% acetic acid, pH 4.7) for an additional 22 h. A microplate reader set at 570 nm was used to determine the absorbance. Results are expressed as the fraction of the optical density determined for cells treated with drug compared to those treated with vehicle.

Propidium Iodide Exclusion Assay 2.5–3.5×10$^5$ SQ-20B cells were cultured in 24-well tissue culture plates for all studies. Cells were treated with varying concentrations of chelerythrine, incubated for 30 min at 37° C. and then irradiated. Radiation was delivered using a $^{60}$Co-irradiator (Gammacell 220, Atomic Energy of Canada) at a dose rate of 2.0 Gy/sec. At the indicated time points, cells were harvested, washed once, and resuspended in PBS containing 50 μl of 100 μg/ml propidium iodide. Viability was analyzed by flow cytometry FACS) on a FACScan (Becton-Dickson) using Lysis II software.

DAPI Staining for Nuclear Visualization

5×10$^5$ SQ-20B cells were centrifuged at 1000 rpm and resuspended in approximately 100 μl of media. The cell suspension was then minced with 100 μl of DAPI (4', 6-iamidino-2-phenylindole, Sigma, 1 μg/ml in PBT [PBS+ 1% Triton X-100]. One drop of this mixture was then placed on a microslide with a coverslip. The cells were viewed by fluorescence microscopy using an Olympus BX-40 microscope with a 100 Watt Mercury lamp, a 16 or 40×Fluorite objective, N.A. 0.75, (Leco #1-UB527) and a UV filter cube (ex 330–385 nm, em 420 nm, wide band pass, Leco #U-M536). Images were photographed using an Optronics cooled low-light video camera (Leco #DEI-470TB) with a 2× coupler (Leco #HR200-CMT). The image was saved to a digital file at 72 dpi for subsequent image processing with Paint Shop Pro 5 (JASC) running on a Windows NT4 workstation.

Growth of Human Tumor Xenografts

SQ-20B (1–5×10$^6$ tumor cells were injected into the right hind limbs of Sprague-Dawley nude mice (Fredrick Cancer Research Institute, Fredrick Md.). Xenografts were grown for 2–3 wk at which time animals were sorted into treatment groups such that the mean tumor volume was 45 mm$^3$+/–4.5 mm$^3$ (SD). At day 0, initial tumor volume was determined by direct measurement with calipers, and tumor volume was deterred and calculated using the equation 1×w$^2$×0.5 (Hallahan et al., 1995). During treatment tumor volumes were measured twice weekly and are presented as percent of original tumor volume. Data are presented as fractional tumor volume +/–SEM. Significance analyzed using the Mann-Whitney Rank Sum Test ($p<0.05$) and denoted in the graphs by "*".

Control mice (n=12) were weighed and injected IP with PBS on days 8, 10, and 12. To determine the proper injection volume, the weight of a mouse (in grams) was divided by 100, and the resulting number (in μl ) was used. Chelerythrine was dissolved in the corresponding volume of PBS. Mice in treatment group 2 (n=10) were injected IP on days 8, 10, and 12 with 5 mg/kg chelerythrine. Treatment group 3 (n=8) mice revere injected IP on days 8, 11, and 14 with 5 mg/kg chelerythrine chloride. Treatment group 4 mice (n=10) were injected IP on days 8, 11, 14, and 17 with 5 mg/kg chelerythrine chloride. Treatment group 4 mice (n=10) were injected IP on days 8, 11, 14, and 17 with 5 mg/kg chelerythrine. Volume was determined on days 8, 10, 13, 15, 17, 21. Body weight was measured on days 8, 9, 10, 11, 12, 13, 14, 15, 16, 17, 18, 21. Each data point represents the mean of 1–3 individual studies (minimum of 8 mice/ treatment groups).

Example 2

Results and Discussion

Chelerythrine Exhibits a Broad Range of Cytotoxic Activity In Vitro

Figure 2A:
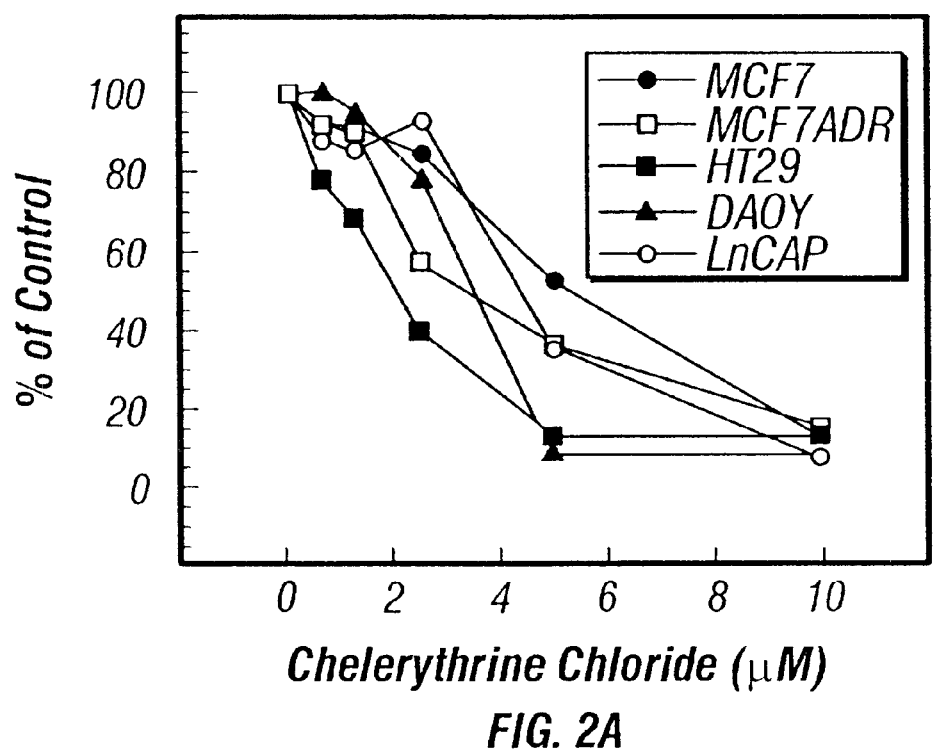
FIGS. 2A–2B. Chelerythrine chloride decreases tumor cell viability.
Figure 2B:
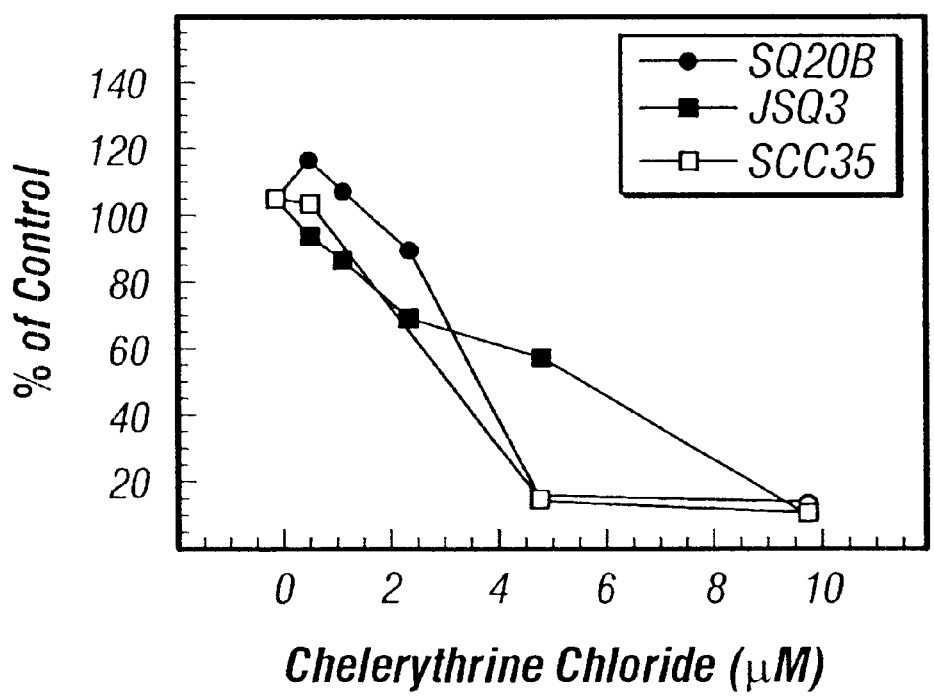

The cytotoxic effects of chelerythrine were evaluated in 9 human tumor cell lines to assess its spectrum of activity. Chelerythrine decreased cell viability as determined by the MTT assay in a dose-dependent manner in MCF7 breast (wt p53)(Blagosklonny et al., 1995), MCF7ADR breast (resistant to adriamycin), HT29 colon (mutant p53)(Shao et al., 1997), DaOY brain (mutant p53)(U et al., 1998), and LnCaP (mutant p53) (Carroll et al., 1993) prostate cells (FIG. 2). The effective dose required to inhibit the growth by 50% of the cells (ED$_{50}$) ranged between 2 and 5 μM upon exposure to drug for 4 h. To assess whether growth inhibition was dependent on exposure time, SQ20B cells were then exposed to increasing concentrations of chelerythrine for 4, 8, 24, 32, 48 and 56 h. Although the ED$_{50}$ decreased from 3.7 to 1.8 μM when cells were exposed for 4 h compared to 8 h, the ED$_{50}$, remained constant up to a 56 h exposure. Equivalent dose-response curves (ED$_{50}$ 4.0–5.2 μM) were found for several radio and/or chemo-resistant oral tumor cell lines including SQ-20B, JSQ-3, and SCC-35 (all mutant p53) (Jung et al., 1992), and for the radiosensitive SCC61 line (wt p53) (Nagasawa et al., 1998; Ramsamooj et al., 1992). The inventors selected the SQ-20B cell line for the subsequent apoptosis studies and animal studies as an example of a radio/chemo resistant human epidennoid carcinoma line (ED$_{50}$ 3.7 μM with chelerythrine) (Brachman et al., 1993; Samuels et al., 1991).

Chelerythrine Induces Apoptosis in p53 Deficient SQ-20B Cells

Figure 3A:
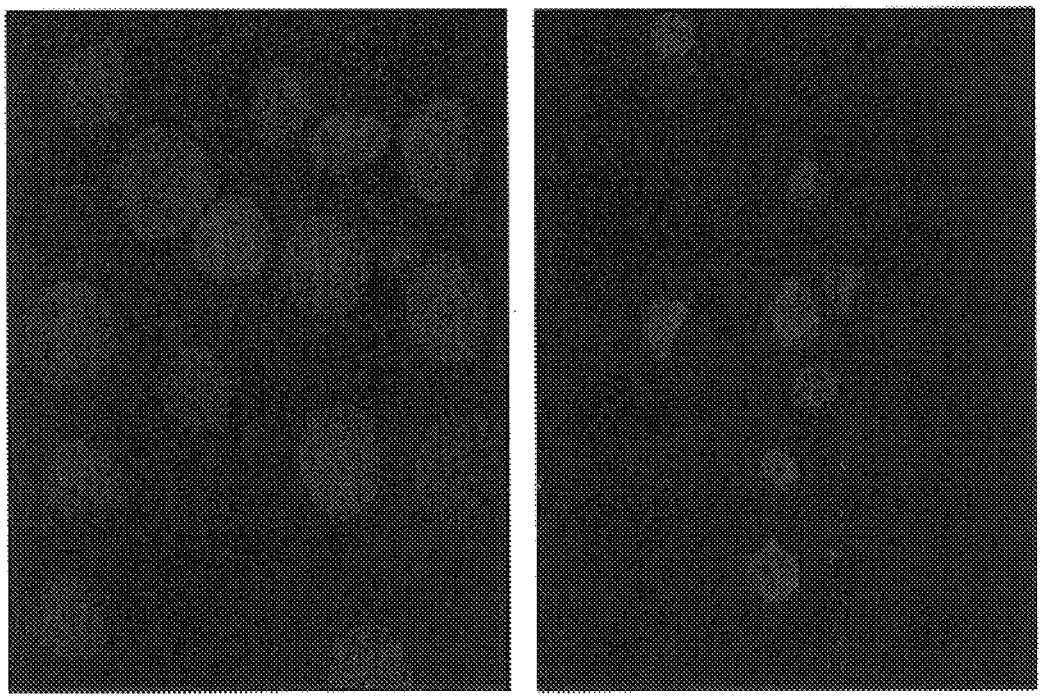
FIGS. 3A–3B. Chelerythrine induces apoptosis in SQ-20B cells in vitro.
Figure 3B:
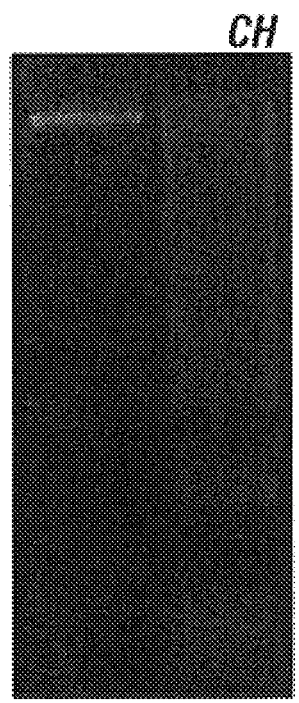

The inventors examined whether the concentrations of chelerythrine that decrease viability in the MTT assay induce apoptosis of SQ-20B cells. The inventors examined cell and nuclear morphology by DAPI staining (FIG. 3). Following exposure of SQ-20B cells to 5 μM chelerythrine, morphological changes consistent with apoptosis were observed (FIG. 3A) in nearly 100% of the cells 72 h following treatment. These data were consistent with the loss of viability as determined by MTT assays. In addition, DNA fragmentation was observed following analysis of low molecular weight DNA by agarose electrophoresis. Clonogenic survival was also decreased following treatment with chelerythrine at these doses. Taken together, these data demonstrate that apoptosis is the principle mechanism of cell death at toxic concentrations of chelerythrine in vitro.

Chelerythrine Exhibits Potent Anti-tumor Activity in SQ-20B Xenografts

Figure 4:
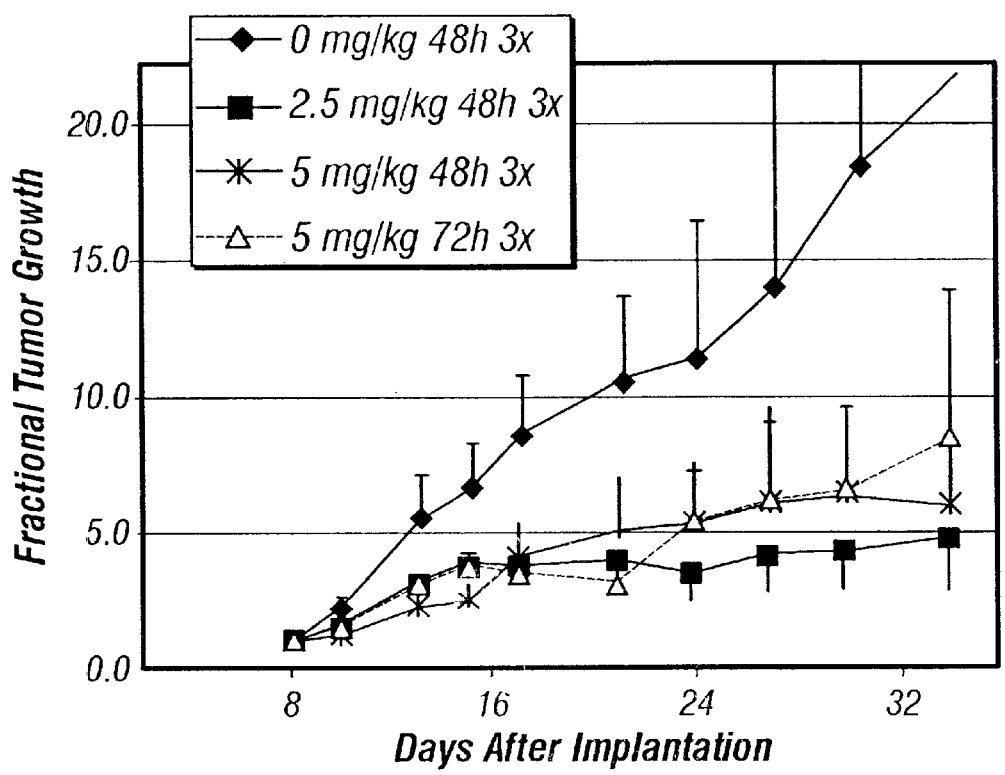

Mice bearing SQ-2QB xenografts (n>8 for all groups) were injected IP with 2.5 mg/kg on days 8, 10, 12 (Group 2, n=10), 5mg/kg on days 8, 10, 12 (Group 3, n=8), and 5 mg/kg on days 8, 11, 14 (Group 4, n=8). As demonstrated in FIG. 4, chelerythrine significantly produced tumor grow delay on day 13 for group 1, on day 10 for group 2, and on day 13 for group 3 ($p<0.05$). By day 21, the mean tumor volumes measured 370 mm$^3$ in control group, 215 mm$^3$ in group 1, 197 mm$^3$ in group 2, and 115 mm$^3$ in group 3. Studies were terminated on day 21 due to tumor burden in the untreated group. The percent change in volume of treated tumors compared to control tumors (%T/C) was found to be less than 40% on day 21 for all treatment groups.

Chelerythrine produced tumor regression in all treatment groups as defined by 2 consecutive tumor measurements that were less than the original volume ($p<0.05$, ANOVA). At no time did body weight of any study animal fall below 90% of the initial weight at the beginning of treatment. There were no treatment related deaths at these concentrations of chelerythrine. Similar results were obtained in two independent studies.

The data demonstrate that chelerythrine is cytotoxic to tumor cell lines regardless of their p53 status. The inventors also show that chelerythrine produces tumor growth inhibition and regression in an HNSCC tumor model of SQ-20B xenografts in mice. The percent change in treated tumor volume compared to control tumors (%TIC), was found to be less than 40% on day 21 for all treatment groups. These data and the finding that body weight is not significantly affected by the treatment regimens suggests that chelerythrine may be a useful anti-tumor agent.

Chelerythrine chloride produces its antineoplastic effect in part through the induction of apoptosis secondary to inhibition of PKC, activation of sphingomyelinase and induction of ceramide production (Chmura et al., 1997; Chmura et al., 1996). Current investigations are underway to delineate the role of apoptosis in contributing to tumor regression in vivo with chelerythrine. 7-hydroxystaurosporine (UNC-01) is a protein kinase inhibitor currently in Phase-1 clinical trials (Gescher, 1998; Sausville et al., 1998). The demonstration that UNC-01 induces anti-tumor effects by mechanisms distinct from those identifies for chelerythrine (Wang et al., 1996) suggest that chelerythrine may exhibit a different spectrum of activity. In addition, the present findings demonstrate the chelerythrine chloride produces antineoplastic effects against diverse histological subtypes of human tumors.

TABLE 1

In vitro Studies with chelerythrine chloride and adriamycin

| 0 ng/mL Adriamycin | 1 ng/mL | 10 ng/mL | 50 ng/mL |
|---|---|---|---|
| 0 | 1 | 1.09 | 0.822 | 0.359 |
| 2 | 0.99 | 0.886 | 0.668 | 0.294 |
| 4 | 0.103 | 0.101 | 0.054 | 0.02 |
| 6 | 0.034 | 0.034 | 0.035 | 0.018 |

Chelerythrine chloride administered in 2, 4, and 6 µM concentrations to SQ20B in vitro showed clonogenic killing (0 ng/mL Adriamycin curve on graph). When used in combination with adriamycin at 1, 10, and 50 ng/mL concentrations, an additive killing effect is seen. For instance, 2 µM chelerythrine chloride and 10 ng/mL of adriamycin has only 0.668 survival when compared to 0.99 with 2 µM chelerythrine alone or 0.822 with 10 ng/mL adriamycin alone. 6 µM chelerythrine chloride appears to be toxic to cells, regardless of how much adriamycin is added.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Aldridge, Arends, Radford, Br. J. Cancer, 71:571–577, 1995.

Ambrosini, Bertoli, Tanfani, Wozniak, Zolese, Chem. Phys. Lipids, 72:127–34, 1994.

Bell and Burns, "Lipid activation of protein kinase C," J. Biol. Chem., 266:4661–4, 1991.

Bertrand et al., Exp. Cell Res., 211:314–321, 1993.

Bertrand, Solary, Kohn, Pommier, Proc. Am. Assoc. Cancer Res., 34:1735, 1994.

Birchall, Bishop, Bradshaw, Cline, Coffey, Elliott, Gibson, Greenham, Hallam, Harris et. al., "Ro 32-0432, a selective and orally active inhibitor of protein kinase C prevents T-cell activation," J. Pharmacol. Exp. Ther., 268:922–9, 1994.

Blagosklonny, Schulte, Nguyen, Mimnaugh, Trepel, Neckers, "Taxol induction of p21WAF1 and p53 requires c-raf-1," Cancer Res., 55:4623–6, 1995.

Blumberg, Cancer Res., 48:1–8, 1988.

Boise, Gottschalk, Quintans, Thompson, Curr. Top Microbiol. Immunol., 200:107–21, 1995.

Boothman, Bouvard, Hughes, Cancer Res., 49:2871–2878, 1989.

Borchardt, Lee, Kalen, Bell, Biochem. Biophys. Acta., 1212:327–36, 1994.

Borek, Pharmacol. Ther., 27:99–142, 1985.

Boring, Squires, Tong, Montgomery, "Cancer statistics," CA Cancer J. Clin., 44:7–26, 1994.

Bose, Verheij, Haimovitz-Friedman, Scotto, Fuks, Kolesnick, Cell, 82:405–14, 1995.

Brachman, Beckett, Graves, Haraf, Vokes, Weichselbaum, "p53 mutation does not correlate with radiosensitivity in 24 head and neck cancer cell lines," Cancer Res., 53:3667–9, 1993.

Bradshaw, Hill, Nixon, Wilkinson, "Therapeutic potential of protein kinase C inhibitors," Agents Actions, 38:135–47, 1993.

Bussink, Tofilon, Brock, Int. J. Radiat. Biol., 70:23–3, 1996.

Carroll, Voeller, Sugars, Gelmann, "p53 oncogene mutations in three human prostate cancer cell lines," Prostate, 23:123–34, 1993.

Chang and Little, Int. J. Radiat. Biol., 60:483–96, 1991.

Chang and Little, Carcinogenesis, 13:923–8, 1992a.

Chang and Little, Radiat. Res., 131:53–9, 1992b.

Chen, Quintans, Fuks, Thompson, Kufe, Weichselbaum, Cancer Res., 55:991–4, 1995.

Chmura, In: Immunology Methods Manual, I. Lefkovits (ed.), Academic Press, 1996.

Chmura, Mauceri, Advani, Heimann, Beckett, Nodzenski, Quintans, Kufe, Weichselbaum, "Decreasing the apoptotic threshold of tumor cells through protein kinase C inhibition and sphingomyelinase activation increases tumor killing by ionizing radiation, Cancer Res., 57:4340–7, 1997.

Chmura, Nodzenski, Crane, Hallahan, Weichselbaum, Quintans, "Cross-talk between ceramide and PKC activity in the control of apoptosis," Adv Exp Med Biol;406:39–55, 1996a.

Chmura, Nodzenski, Quintans, Weischelbaum, "PKC inhibition induces apoptosis and ceramide production through a neutral sphingomyelinase," Cancer Res., 56:2711–2714, 1996b.

Choi, Boise, Gottschalk, Quintans, Thompson, Klaus, Eur. J. Immunol., 25:1352–7, 1995.

Coroneos et al., J. Biol. Chem. 270:23305–23309, 1995

Cotter, Lennon, Clynn, Green, Cancer Res., 52:997–1005, 1992.

Cuvillier, Pirianov, Kleuser, Vanek, Coso, Spiegel, Nature, 381:800–803, 1996.

Datta, Banach, Kojima, Talanian, Alnemri, Wong, Kufe, Blood, 88:1936–43, 1996.

Datta, Manome, Taneja, Boise, Weichselbaum, Thompson, Slapak, Kufe, *Cell Growth Differ.,* 6:363–370, 1995.

Datta, R. et al., *J. Biol. Chem.* 272:1965–1969, 1997.

Dewey, Ling, Meyn, *Int. J. Radiat. Oncol. Biol. Phys.,* 33:781–96, 1995.

Donaldson, Goolsby, Kiener, Wahl, "Activation of p34cdc2 coincident with taxol-induced apoptosis," *Cell Growth Differ.,* 5:1041–50, 1994.

Dressler and Kolesnick, *J. Biol. Chem.,* 265:14921–14917, 1990.

Dressler, Mathias, Kolesnick, *Science,* 255:1715–18, 1992.

Emoto, Manome, Meinhardt, Kisaki, Kharbanda, Robertson, Ghayur, Wong, Kamen, Weichselbaum, et al., *EMBO J.,* 14:6148–56, 1995.

Forbes et al., *Exp. Cell Res.,* 198:367–371, 1992.

Fuks, Persaud, Alfieri, McLoughlin, Ehleiter, Schwartz, Seddon, Cordon-Cardo, Haimovitz-Friedman, *Cancer Res.,* 54:2582–2590, 1994.

Gescher, "Analogs of staurosporine: potential anticancer drugs?", *Gen. Pharmacol.,* 31:721–8, 1998.

Gomez-Munoz, Martin, O'Brien, Brindley, *J. Biol. Chem.,* 269:18384–9, 1994.

Gorczyca et al., *Cancer Res.,* 53: 1945–1951, 1993.

Gottschalk and Quintans, "Apoptosis in B lymphocytes: the WEHI-231 perspective," *Immunol. Cell Biol.,* 73:8–16, 1995a.

Gottschalk and Quintans, *Immunol. Cell Biol.,* 73:41–49, 1995b.

Gottschalk, Boise, Thompson, Quintans, *Proc. Natl. Acad. Sci. USA,* 91:7350–4, 1994.

Gottschalk, McShan, Kilkus, Dawson, Quintans, "Resistance to anti-IgM-induced apoptosis in a WEHI-231 subline is due to insufficient production of ceramide," *Eur. J. Immunol.,* 25:1032–8, 1995.

Gottschalk, McShan, Merino, Quintans, *Inter. Immun.,* 6:121–30, 1993.

Grant, Turner, Bartimole, Nelms, Joe, Jarvis, "Modulation of 1-[beta-D-arabinofuranosyl] cytosine-induced apoptosis in human myeloid leukemia cells by staurosporine and other pharmacological inhibitors of protein kinase C,". *Oncol. Res.,* 6:87–99, 1994.

Gray et al., *Planta Medica* 39:209, 1980.

Gupta, Gomez-Munoz, Matowe, Brindley Ginsberg, "Thyroid-stimulating hormone activates phospholipase D in FRTL-5 thyroid cells via stimulation of protein kinase C," *Endocrinology,* 136:3794–9, 1995.

Haggerty and Monroe, *Cell. Immun.,* 154:166–80, 1994.

Haimovitz-Friedman, Kan, Ehleiter, Persaud, McLoughlin, Fuks, Kolesnick, "Ionizing radiation acts on cellular membranes to generate ceramide and initiate apoptosis," *J. Exp. Med.,* 180:525–35, 1994a.

Haimovitz-Friedman, Balaban, McLoughlin, Ehleiter, Michaeli, Vlodavsky, Fuks, *Cancer Res.,* 54:2591–7, 1994b.

Hall, *Radiobiology for the Radiologist*, Harper and Row, 1988.

Hall, *Radiobiology for the Radiologist*, Harper and Row, 1994.

Hallahan, Beckett, Kufe, et al., *Int. J. Rad. Onc. Biol.,* 19:69–74, 1990.

Hallahan, Dunphy, Virudachalam, Sukhatme, Kufe, Weichselbaum, "C-jun and Egr-1 participate in DNA synthesis and cell survival in response to ionizing radiation exposure," *J. Biol. Chem.,* 270:30303–30309, 1995.

Hallahan, Virudachalam, Kuchibhotla, Kufe, Weichselbaum, *Proc. Natl. Acad. Sci. USA,* 91:4897–901, 1994.

Hallahan, Virudachalam, Schwartz, Panje, Mustafi, Weischselbaum, *Radiat. Res.,* 129:345–50, 1992.

Hannun and Linardic, "Sphingolipid breakdown products: anti-proliferative and tumor-suppressor lipids," *Biochim. Biophys. Acta.,* 1154:223–36, 1993.

Hansen, Nielsen, Berg, "RE-examination and further development of rapid dye method for measuring cell growth/cell kill," *J. Immunol. Methods,* 119:203–210, 1989.

Harmon and Allan, *Scanning Microsc.,* 2:561–8, 1988.

Herbert, Augereau, Gleye, Maffrand, "Chelerythrine is a potent and specific inhibitor of protein kinase C," *Biochem. Biophys. Res. Commun.,* 172:993–9, 1990.

Horton, Srivastava, Smudzka, Wilson, *Nucleic Acids Res.,* 23:3810–5, 1995.

Hu and Fan, "Protein kinase C inhibitor calphostin C prevents cytokine-induced angiogenesis in the rat," *Inflammation,* 19:39–54, 1995.

Indap and Rao, *Natl. Med. J. India,* 8:65–7, 1995.

Jacobsen, Weil, Raff, "Role of Ced-3/ICE-family proteases in staurosporine-induced programmed cell death," *J. Cell. Biol.,* 133:1041–51, 1996.

Jacobson, Burne, Raff, "Programmed cell death and Bcl-2 protection in the absence of a nucleus," *Embo. J.,* 13:1899–910, 1994.

Jarvis and Kolesnick, *Clinical. Cancer Research,* 2:1–6, 1996.

Jarvis W. D., Fornari F. A., Traylor R. S., Martin H. A., Kramer L. B., Erukulla R. K., Bittman R, Grant S, "Induction of apoptosis and potentiation of ceramide-mediated cytotoxicity by sphingoid bases in human myeloid leukemia cells," *J. Biol Chem,* Apr 5;271(14): 8275–84, 1996.

Jarvis, Kolesnick, Fornari, Traylor, Gewirtz, Grant, *Proc. Natl. Acad. Sci. USA,* 91:73–77, 1994.

Jarvis, Turner, Povirk, Traylor, Grant, "Induction of apoptotic DNA fragmentation and cell death in HL-60 human promyelocytic leukemia cells by pharmacological inhibitors of protein kinase C," *Cancer Res.,*" 54:1707–14, 1994.

Ji, Zhang, Hirabayashi, *Biochem. Biophys. Res. Commun.,* 212:640–7, 1995.

Jones and Murray, *J. Biol. Chem.,* 270:5007–13, 1995. Jung, Notario, Dritschilo, "Mutations in the p53 gene in radiation-sensitive and-resistant human squamous carcinoma cells," *Cancer Res.,* 52:6390–3, 1992.

Kharbanda, Ren, Pandey, Shafinan, Kyriakis, Weichselbaum, Kufe, *Nature,* 376:375–8, 1995.

Knox, Johnson, Gordon, "A study of protein kinase C isozyme distribution in relation to Bcl-2 expression during apoptosis of epithelial cells in vivo," *Exp. Cell Res.,* 207:68–73, 1993.

Kobayashi, Ando, Nakano, Iida, Ohno, Morimoto, Tamaoki, "Calphostins (UCN-1028), novel and specific inhibitors of protein kinase C. I. Fermentation, isolation, physico-chemical properties and biological activities," *J. Antibiot.,* (Tokyo), 42:1470–4, 1989.

Kobayashi, Nakano, Morimito, Tamaoki, *Biochem. Biophys. Res. Commun.,* 159:548–53, 1989.

Kolesnick, Haimovitz-Friedman, Fuks, *Biochem. Cell. Biol.,* 72:471–4, 1994.

Kolesnick, *J. Biol. Chem.,* 264:7617–23, 1989.

Kolesnick, *Mol. Chem. Neuropathol.,* 21:287–97, 1994.

Kondratyev, Chung, Jung, *Cancer Res.,* 56:1498–1502, 1996.

Lambert and Borek, *J. Natl. Cancer Inst.,* 80:1492–1497, 1988.

Long, et al., *J. Clin. Invest.,* 82:1779, 1988.

Lowe et al., *Science*, 266:807–10, 1994.

Lowe, Ruley, Jacks, Housman, *Cell*, 74:957–67, 1993a.

Lowe, Schmitt, Smith, Osborne, Jacks, *Nature*, 362:847–9, 1993b.

Lozano, Berra, Municio, Diaz-Meco, Dominguez, Sanz, Moscat, *J. Biol. Chem.*, 269:19200–07, 1994.

Magnuson et. al., *Semin. Cancer Biol.*, 5:277–284, 1994.

Maity, McKenna, Muschel, *Radiother. Oncol.*, 31:1–13, 1994.

Martin and Green, *Curr. Opin. Oncol.*, 6:616–21, 1994.

Martin, Newmeyer, Mathias, Farschon, Wang, Reed, Kolesnick, Green, *Embo J.*, 14:5191–200, 1995.

May, Tyler, Ito, Armstrong, Qatsha, Davidson, "Interleukin-3 and bryostatin-1 mediate hyperphosphorylation of BCL2 alpha in association with suppression of apoptosis," *J. Biol. Chem.*, 269:26865–70, 1994.

McConkey, Hartzell, Jondal, Orrenius, "Inhibition of DNA fragmentation in thymocytes and isolated thymocyte nuclei by agents that stimulate protein kinase C," *J. Biol. Chem.*, 264:13399–402, 1989.

McKenna, Iliakis, Weiss, Bernhard, Muschel, *Radiat. Res.*, 125:283–7, 1991.

Meyn et. al., *Radiat. Res.*, 136:327–34, 1993.

Meyn, Stephens, Hunter, Ang, Milas, *Int. J. Radiat. Oncol. Biol. Phys.*, 30:619–624, 1994.

Meyn, Stephens, Hunter, Milas, *Anticancer Drugs*, 6:443–50, 1995.

Nagasawa, Keng, Harley, Dahlberg, Little, *Int. J. Radiat. Biol.*, 66:373–379, 1994.

Nagasawa, Keng, Maki, Yu, Little, "Absence of a radiation-induced first-cycle Gl-S arrest in p53+ human tumor cells synchronized by mitotic selection," *Cancer Res.*, 58:2036–41, 1998.

Nagata and Golstein, *Science*, 267:1449–52, 1995.

Nixon, Bishop, Wilkinson, "The design of biological properties of selective inhibitors of protein kinase C," *Second Messenger Systems*, 1992.

Obeid, Linardic, Karolak, Hannun, *Science*, 259:1769–71, 1993.

Ohta, Yatomi, Sweeney, Hakomori Igarashi, "A possible role of sphingosine in induction of apoptosis by tumor necrosis factor-alpha in human neutrophils," *FEBS Lett.*, 355:267–70, 1994.

Ojeda, Guarda, Maldonato, Folch, *Cell. Inmunol.*, 125:535–539, 1990.

Osmani, McGuire, Osmani, "Parallel activation of the NIMA and p34cdc2 cell cycle-regulated protein kinases is required to initiate mitosis in A. nidulans," *Cell*, 67:283–91, 1991.

Park, *J. Biol. Chem.*, 270:15467–15470, 1995.

Preiss, Loomis, Bishop, Stein, Niedel, Bell, *J. Biol. Chem.*, 261: 8597–600, 1986.

Quintans, Kilkus, McShan, Gottschalk, Dawson, *Biochem. Biophys. Res. Commun.*, 202:710–4, 1994.

Radford and Murphy, *Int. J. Radiat. Biol.*, 65:229–39, 1994.

Raff, Barres, Burne, Coles, Ishizaki, Jacobson, "Programmed cell death and the control of cell survival," *Philos. Trans. R. Soc. Lond. B. Biol. Sci.*, 345:265–8, 1994.

Ramsamooj, Kasid, Dritschilo, "Differential expression of proteins in radioresistant and radiosensitive human squamous carcinoma cells," *J. Natl. Cancer Inst.*, 84:622–8, 1992.

Rosenthal et. al., *Semin. Oncol.*, 22:13–17, 1995.

Rotenberg, Huang, Zhu, Su, Riedel, "Deletion analysis of protein kinase C inactivation by calphostin C," *Mol. Carcinog.*, 12:42–9, 1995.

Rotenberg, Zhu, Su, Riedel, *Mol. Carcin.*, 12:42–9, 1995.

Samuels, Murray, Cohen, Safa, Sinha, Townsend, Beckett, Weichselbaum, "Increased glutathione peroxidase activity in a human sarcoma cell line with inherent doxorubicin resistance," *Cancer Res.*, 57:521–7, 1991.

Sanchez and Elledge, *Bioessays*, 17:545–8, 1995.

Santana et. al., *Cell*, 88:189–199, 1996.

Sausville, Lush, Headlee, Smith, Figg, Arbuck, Senderowicz, Fuse, Tanii, Kuwabara, Kobayashi, "Clinical pharmacology of UCN-01: initial observations and comparison to preclinical models," *Cancer Chemother. Pharmacol.*, 42:554–9, 1998

Schroter, Peitsch, Tschopp, "Increased p34cdc2-dependent kinase activity during apoptosis: a possible activation mechanism of DNase I leading to DNA breakdown," *Eur. J. Cell Biol.*, 69:143–50,1996.

Schwartz, Haimovitz-Friedman, Dhupar, Ehleiter, Maslak, Lai, Loganzo, Jr., Kelsen, Fuks, Albino, "Potentiation of apoptosis by treatment with the protein kinase C-specific inhibitor safingol in mitomycin C-treated gastric cancer cells," *J. Natl. Cancer Inst.*, 87:1394–9, 1995.

Shao, Cao, Shimizu, O'Connor, Kohn, Pommier, "Abrogation of an S-phase checkpoint and potentiation of camptothecin cytotoxicity by 7-hydroxystaurosporine (UCN-01) in human cancer cell lines, possibly influenced by p53 function," *Cancer Res.*, 57:4029–35, 1997.

Shen, Cloud, Chen, Park, *J. Biol. Chem.*, 271:148–152, 1996.

Shi, Nishioka, Th'ng, Bradbury Litchfield, Greenberg, "Premature p34cdc2 activation required for apoptosis," [see comments], *Science*, 263:1143–5, 1994.

Shirahama, Sakakura, Sweeney, Ozawa, Takemoto, Nishiyama, Ohi, Igarashi, "Sphingosine induces apoptosis in androgen-independent human prostaticcarcinoma DU-145 cells by suppression of bcl-X(L) gene expression," *FEBS Lett.*, 407:97–100, 1997.

Stephens, Ang, Schultheiss, Milas, Meyn, *Radiation Research*, 127:308–136, 1991.

Stephens, Hunter, Ang, Milas, Meyn, *Radiat. Res.*, 135, 75–80, 1993.

Strum, Small, Pauig, Daniel, *J. Biol Chem.*, 269:15493–7, 1994.

Szumiel, *Int. J Radiat. Biol.*, 66:329–41, 1994.

Thompson and Fields, *J. Biol. Chem.*, 271:15045–15053, 1996.

U, Banaie, Rigby, Chen, "Mutant p53 may selectively suppress glial specific proteins in pluripotential human neuroectodermal tumor cells," *Neurosci. Lett.*, 244:41–6, 1998.

Uckun, Evans, Forsyth, Waddick, Ahlgren, Chelstrom, Burkhardt, Bolen, Myers, *Science*, 267:886–91, 1995.

Venable, Blobe, Obeid, *J. Biol. Chem.*, 269:26040–9, 1994.

Verheij, Haimovitz-Friedman, Fuks, Kolesnick, *Nature*, 380:75–78, 1996.

Vokes and Weichselbaum, *J. Clin. Oncol.*, 8:911–34, 1990.

Vokes, Weichselbaum, Lippman, Hong, "Head and neck cancer,", *N. Engl. J. Med.*, 328:18–94, 1993.

Wang, Saijun, Eastman, Worland, Sausville, O'Connor, "UNC-01: a Potent Abrogator of G2 Checkpoint Function in Cancer Cells with Disrupted p53," *J. Natural Cancer Inst.*, 88:956–962, 1996.

Weil, Jacobson, Coles, Davies, Gardner, Raff, Raff, "Constitutive expression of the machinery for programmed cell death," *J. Cell Biol.*, 133:1053–9, 1996.

Wiegmann, Schutze, Machleidt, Witte, Kronke, *Cell*, 78:1005–15, 1994.

Witte, Fuks, Haimovitz-Friedman, Vlodavsky, Goodman, Eldor, *Cancer Res.*, 49:5066–5072, 1989.

Young, Murtha, Zhang, *Oncol. Res.*, 6:203–10, 1994.

What is claimed is:

1. A method for inhibiting the growth of a cell comprising contacting said cell with chelerythrine and a chemotherapeutic DNA damaging agent, wherein the dose of chelerythrine, when combined with the dose of said DNA damaging agent, is effective to inhibit growth of said cell.

2. The method of claim 1, wherein chelerythrine is contacted with said cell prior to contacting said cell with said DNA damaging agent.

3. The method of claim 1, wherein said DNA damaging agent is contacted with said cell prior to contacting said cell with chelerythrine.

4. The method of claim 1, wherein said cell is a cancer cell.

5. The method of claim 4, wherein said cancer cell is a bladder cancer cell, a blood cancer, a breast cancer cell, a lung cancer cell, a colon cancer cell, a prostate cancer cell, a liver cancer cell, a pancreatic cancer cell, a stomach cancer cell, a testicular cancer cell, a brain cancer cell, an ovarian cancer cell, a lymphatic cancer cell, a skin cancer cell, a brain cancer cell, a bone cancer cell, a soft tissue cancer cell.

6. The method of claim 1, wherein said cell is located in a human subject.

7. The method of claim 6, wherein chelerythrine is administered by direct intratumoral injection.

8. The method of claim 6, wherein chelerythrine is administered by injection into tumor vasculature.

9. The method of claim 1, wherein said DNA damaging agent is from a group consisting of doxorubicin, daunorubicin, dactinomycin, mitoxantrone, cisplatin, procarbazine, mitomycin, carboplatin, bleomycin, etoposide, teniposide, mechlroethamine, cyclophosphamide, ifosfamide, melphalan, chlorambucil, ifosfamide, melphalan, hexamethylmelamine, thiopeta, busulfan, carnustine, lomustine, semustine, streptozocin, dacarbazine, adriamycin, 5-fluorouracil (5FU), camptothecin, actinomycin-D, hydrogen peroxide, nitrosurea, plicomycin, tamoxifen, taxol, transplatinum, vincristin, vinblastin and methotrexate.

10. The method of claim 1, wherein said cell is contacted with chelerythrine a second time.

11. The method of claim 1, wherein said cell is contacted with said DNA damaging agent a second time.

12. The method of claim 1, wherein chelerythrine and said DNA damaging agent are contacted with said cell within about 4 days.

13. The method of claim 12, wherein chelerythrine and said DNA damaging agent are contacted with said cell within about 3 days.

14. The method of claim 13, wherein chelerythrine and said DNA damaging agent are contacted with said cell within about 2 days.

15. The method of claim 14, wherein chelerythrine and said DNA damaging agent are contacted with said cell within about 1 day.

16. The method of claim 15, wherein chelerythrine and said DNA damaging agent are contacted with said cell within about 12 hours.

17. The method of claim 16, wherein chelerythrine and said DNA damaging agent are contacted with said cell within about 6 hours.

18. The method of claim 17, wherein chelerythrine and said DNA damaging agent are contacted with said cell within about 2 hours.

19. The method of claim 18, wherein chelerythrine and said DNA damaging agent are contacted with said cell within about 1 hour.

20. The method of claim 1, wherein chelerythrine and said DNA damaging agent are contacted with said cell at the same time.

21. The method of claim 1, further comprising tumor resection.

22. The method of claim 21, wherein said tumor resection occurs prior to said contacting.

23. The method of claim 22, wherein said contacting comprising treating said resected tumor bed with chelerythrine and said DNA damaging agent.

24. The method of claim 21, wherein said tumor resection occurs after said contacting.

25. The method of claim 21, wherein said contacting occurs both before and after said tumor resection.

26. The method of claim 1, wherein said dose of chelerythrine is about 0.5 mg/kg to about 10 mg/kg.

27. The method of claim 26, wherein said dose of chelerythrine is about 1 mg/kg to about 4 mg/kg.

28. A method of killing a cell comprising contacting said tumor cell with chelerythrine and a chemotherapeutic DNA damaging agent, wherein the dose of said chelerythrine, when combined with the dose of said DNA damaging agent, is effective to kill said tumor cell.

29. A method of treating cancer in a human patient comprising administering chelerythrine and a chemotherapeutic DNA damaging agent to said human patient, wherein the dose of said chelerythrine, when combined with the dose of said DNA damaging agent, is effective to treat said cancer.

30. A method of potentiating the effect of a chemotherapeutic DNA damaging agent on a tumor cell comprising contacting said tumor cell with chelerythrine and then contacting said tumor cell with said DNA damaging agent.

* * * * *